(12) United States Patent
Meyerson et al.

(10) Patent No.: US 9,499,856 B2
(45) Date of Patent: Nov. 22, 2016

(54) DDR2 MUTATIONS IN SQUAMOUS CELL LUNG CANCER

(71) Applicant: The Broad Institute, Inc., Cambridge, MA (US)

(72) Inventors: Matthew Meyerson, Concord, MA (US); Peter Hammerman, Jamaica Plain, MA (US); Alexis Ramos, Somerville, MA (US)

(73) Assignees: The Board Institute, Inc., Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 200 days.

(21) Appl. No.: 13/875,079

(22) Filed: May 1, 2013

(65) Prior Publication Data

US 2013/0261017 A1 Oct. 3, 2013

Related U.S. Application Data

(63) Continuation of application No. PCT/US2013/030292, filed on Mar. 11, 2013.

(60) Provisional application No. 61/619,273, filed on Apr. 2, 2012.

(51) Int. Cl.
*C12Q 1/68* (2006.01)
*C12P 19/34* (2006.01)
*A61K 48/00* (2006.01)

(52) U.S. Cl.
CPC .............. *C12Q 1/68* (2013.01); *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2005/0186571 A1 | 8/2005 | Ullrich et al. |
| 2007/0237770 A1 | 10/2007 | Lai et al. |
| 2008/0031893 A1 | 2/2008 | Tripp et al. |
| 2008/0171045 A1 | 7/2008 | Lewicki et al. |
| 2009/0208461 A1 | 8/2009 | Hotz et al. |
| 2010/0068207 A1 | 3/2010 | Fanidi |
| 2010/0216718 A1 | 8/2010 | Rikova |
| 2011/0287011 A1 | 11/2011 | Gurney et al. |
| 2011/0287037 A1 | 11/2011 | Gentschev et al. |
| 2012/0065233 A1 | 3/2012 | Gregor et al. |

FOREIGN PATENT DOCUMENTS

| | | | | |
|---|---|---|---|---|
| KR | 10-2007-0012648 | 1/2007 | ......... | C07D 491/048 |
| WO | WO 2005/092896 | 10/2005 | ......... | C07D 491/048 |

OTHER PUBLICATIONS

Juppner, Bone, 1995, vol. 17, 39S-42S.*
Hegele, Arterioscler. Thromb. Vasc. Biol, 2002,vol. 22, pp. 1058-1061.*
Ionnidis (Plost Med, 2005, 2(8):e124).*
Dermer, G.B. (Bio/Technology (1994) 12: 320).*
Sos (Oncogene, 2012, 31:4811-4814).*
International Preliminary Report on Patentability in International Application No. PCT/US2013/030292, issued Oct. 7, 2014, 7 pages.
Ali et al., "Trafficking defects and loss of ligand binding are the underlying causes of all reported DDR2 missense mutations found in SMED-SL patients," Hum. Mol. Genet., 19(11):2239-2250 (2010).
Bargal et al., "Mutations in DDR2 gene cause SMED with short limbs and abnormal calcifications," Am. J. Hum. Genet., 84(1):80-84 (2009).
Bass et al., "SOX2 is an amplified lineage-survival oncogene in lung and esophageal squamous cell carcinomas," Nat. Genet., 41(11):1238-1242 (2009) (Author Manuscript).
Beroukhim et al., "The landscape of somatic copy-number alteration across human cancers" Nature, 463(7283):899-905 (2010) (Author Manuscript).
Davies et al., "Somatic mutations of the protein kinase gene family in human lung cancer," Cancer Res., 65(17):7591-7595 (2005).
Day et al., "Inhibition of collagen-induced discoidin domain receptor 1 and 2 activation by imatinib, nilotinib and dasatinib," Eur. J. Pharmacol., 599(1-3):44-53 (2008).
Du et al., "Bead-based profiling of tyrosine kinase phosphorylation identifies SRC as a potential target for glioblastoma therapy," Nat. Biotechnol., 27(1):77-83 (2009).
Ford et al., "Expression and mutation analysis of the discoidin domain receptors 1 and 2 in non-small cell lung carcinoma," Br. J. Cancer, 96(5):808-814 (2007).
Hammerman et al., "Resistance to Epidermal Growth Factor Receptor Tyrosine Kinase Inhibitors in Non-Small Cell Lung Cancer," Clin. Cancer Res., 15(24):7502-7509 (2009).
Haura et al., "Phase I/II study of the Src inhibitor dasatinib in combination with erlotinib in advanced non-small-cell lung cancer," J. Clin. Oncol., 28(8):1387-1394 (2010).
Hennequin et al., "Novel 4-anilinoquinazolines with C-6 carbon-linked side chains: synthesis and structure-activity relationship of a series of potent, orally active, EGF receptor tyrosine kinase inhibitors," Bioorg. Med. Chem. Lett., 16(10):2672-2676 (2006).
Higgins and Ettinger, "Chemotherapy for lung cancer: the state of the art in 2009," Expert Rev. Anticancer Ther., 9:1365-1378 (2009).
Ikeda et al., "Discoidin domain receptor 2 interacts with Src and Shc following its activation by type I collagen," J. Biol. Chem., 277(21):19206-19212 (2002).
Johnson et al., "Phase II study of dasatinib in patients with advanced non-small-cell lung cancer," J. Clin. Oncol., 28(30):4609-4615 (2010).
Kan et al., "Diverse somatic mutation patterns and pathway alterations in human cancers," Nature, 466(7308):869-873 (2010).
Karaman et al., "A quantitative analysis of kinase inhibitor selectivity," Nat. Biotechnol., 26(1):127-132 (2008).
Kim et al., "Dasatinib in solid tumors," Expert Opin. Investig. Drugs, 19(3):415-425 (2010).
Kotz, J., "The DDR is in," SciBX, 4(20): doi:10.1038/scibx.2011.559 Published online May 19, 2011, 4 pages.
Labrador et al., "The collagen receptor DDR2 regulates proliferation and its elimination leads to dwarfism," EMBO Rep., 2(5):446-452 (2001).
Leitinger B., "Molecular analysis of collagen binding by the human discoidin domain receptors, DDR1 and DDR2. Identification of collagen binding sites in DDR2," J. Biol. Chem., 278(19):16761-16769 (2003).

(Continued)

*Primary Examiner* — Sarae Bausch
(74) *Attorney, Agent, or Firm* — Fish & Richardson P.C.

(57) ABSTRACT

Methods for treating patients with squamous cell lung cancer, including detecting the presence of mutations in the discoidin domain receptor 2 (DDR2) gene.

24 Claims, 16 Drawing Sheets

(56) References Cited

OTHER PUBLICATIONS

Lennes et al., "Quality indicators in cancer care: development and implementation for improved health outcomes in non-small-cell lung cancer," Clin. Lung Cancer, 10(5):341-346 (2009).
Li et al., "A chemical and phosphoproteomic characterization of dasatinib action in lung cancer," Nat. Chem. Biol., 6(4):291-299 (2010) (Author Manuscript).
Lynch et al., "Activating mutations in the epidermal growth factor receptor underlying responsiveness of non-small-cell lung cancer to gefitinib," N. Engl. J. Med., 350(21):2129-2139 (2004).
Manley et al., "Extended kinase profile and properties of the protein kinase inhibitor nilotinib," Biochim. Biophys. Acta., 1804(3):445-453 (2010).
McDermott et al., "Genomic alterations of anaplastic lymphoma kinase may sensitize tumors to anaplastic lymphoma kinase inhibitors," Cancer Res., 68(9):3389-3395 (2008).
Mok et al., "Gefitinib or carboplatin-paclitaxel in pulmonary adenocarcinoma," N. Engl. J. Med., 361(10):947-957 (2009).
Nosaka et al., "STAT5 as a molecular regulator of proliferation, differentiation and apoptosis in hematopoietic cells," EMBO J., 18(17):4754-4765 (1999).
O'Hare et al., "AP24534, a pan-BCR-ABL inhibitor for chronic myeloid leukemia, potently inhibits the T315I mutant and overcomes mutation-based resistance," Cancer Cell, 16(5):401-412 (2009).
Ohashi and Pao, "A New Target for Therapy in Squamous Cell Carcinoma of the Lung," Cancer Discovery, published on Apr. 14, 2011 as doi:10.1158/2159-8274.CD-11-0069.
Olaso et al., "Discoidin domain receptor 2 regulates fibroblast proliferation and migration through the extracellular matrix in association with transcriptional activation of matrix metalloproteinase-2," J. Biol. Chem., 277(5):3606-3613 (2002).
Paez et al., "EGFR mutations in lung cancer: correlation with clinical response to gefitinib therapy," Science, 304(5676):1497-500 (2004).
Pao et al., "Acquired resistance of lung adenocarcinomas to gefitinib or erlotinib is associated with a second mutation in the EGFR kinase domain," PLoS Med., 2(3):e73, 11 pages (2005).
Quintas-Cardama et al., "Imatinib and beyond—exploring the full potential of targeted therapy for CML," Nat. Rev. Clin. Oncol., 6(9):535-543 (2009).
Ramos et al., "Amplification of chromosomal segment 4q12 in non-small cell lung cancer," Cancer Biol. Ther., 8(21):2042-2050 (2009).
Raponi et al., "Gene expression signatures for predicting prognosis of squamous cell and adenocarcinomas of the lung," Cancer Res., 66(15):7466-7472 (2006).
Rikova et al., "Global survey of phosphotyrosine signaling identifies oncogenic kinases in lung cancer," Cell, 131(6):1190-203 (2007).
Sasaki et al., "The biology and treatment of EML4-ALK non-small cell lung cancer," Eur. J. Cancer, 46(10):1773-80 (2010) (Author Manuscript).
Shaw et al., "Clinical features and outcome of patients with non-small-cell lung cancer who harbor EML4-ALK," J. Clin. Oncol., 27(26):4247-4253 (2009).
Shigematsu et al., "Clinical and biological features associated with epidermal growth factor receptor gene mutations in lung cancers," J. Natl. Cancer Inst., 97(5):339-346 (2005).
Shrivastava et al., "An orphan receptor tyrosine kinase family whose members serve as nonintegrin collagen receptors," Mol. Cell., 1(1):25-34 (1997).
Song et al., "Dasatinib (BMS-354825) selectively induces apoptosis in lung cancer cells dependent on epidermal growth factor receptor signaling for survival," Cancer Res., 66(11):5542-5548 (2006).
Sos et al., "Predicting drug susceptibility of non-small cell lung cancers based on genetic lesions," J. Clin. Invest., 119(6):1727-1740 (2009).
Stegmeier et al., "Targeted cancer therapies in the twenty-first century: lessons from imatinib," Clin. Pharmacol. Ther., 87(5):543-552 (2010).
Tomasson et al., "Somatic mutations and germline sequence variants in the expressed tyrosine kinase genes of patients with de novo acute myeloid leukemia," Blood, 111(9):4797-808 (2008).
Tonon et al., "High-resolution genomic profiles of human lung cancer," Proc. Natl. Acad. Sci. USA, 102(27):9625-9630 (2005).
Vogel et al., "The discoidin domain receptor tyrosine kinases are activated by collagen," Mol. Cell., 1(1):13-23 (1997).
Vogel et al., "Discoidin domain receptor 1 is activated independently of $\beta_1$ integrin," J. Biol. Chem., 275(8):5779-84 (2000).
Vogel et al., "Discoidin domain receptor 1 tyrosine kinase has an essential role in mammary gland development," Mol. Cell. Biol., 21(8):2906-2917 (2001).
Vogel, "Discoidin domain receptors: structural relations and functional implications," FASEB J., 13 Suppl:S77-82 (1999).
Weiss et al., "Frequent and focal FGFR1 amplification associates with therapeutically tractable FGFR1 dependency in squamous cell lung cancer," Sci. Transl. Med., 2(62):62ra93, 18 pages (2010) (Author Manuscript).
West et al., "Histologic considerations for individualized systemic therapy approaches for the management of non-small cell lung cancer," Chest, 136(4):1112-1118 (2009).
International Search Report and the Written Opinion of the International Searching Authority for International Application No. PCT/US2013/030292 dated Jun. 14, 2013.
Hammerman, P. S. et al. "Mutations in the DDR2 Kinase Gene Identify a Novel Therapeutic Target in Squamous Cell Lung Cancer" Cancer Discovery, vol. 1, No. 1, pp. 78-89 (2011).

* cited by examiner

FIG. 1C

SEQUENCE LISTING

<160> NUMBER OF SEQ ID NOS: 11

<210> SEQ ID NO 1
<211> LENGTH: 855
<212> TYPE: PRT
<213> ORGANISM: Homo sapiens

<400> SEQUENCE: 1

Met Ile Leu Ile Pro Arg Met Leu Leu Val Leu Phe Leu Leu Leu Pro
 1               5                   10                  15

Ile Leu Ser Ser Ala Lys Ala Gln Val Asn Pro Ala Ile Cys Arg Tyr
            20                  25                  30

Pro Leu Gly Met Ser Gly Gly Gln Ile Pro Asp Glu Asp Ile Thr Ala
        35                  40                  45

Ser Ser Gln Trp Ser Glu Ser Thr Ala Ala Lys Tyr Gly Arg Leu Asp
50                  55                  60

Ser Glu Glu Gly Asp Gly Ala Trp Cys Pro Glu Ile Pro Val Glu Pro
65                  70                  75                  80

Asp Asp Leu Lys Glu Phe Leu Gln Ile Asp Leu His Thr Leu His Phe
                85                  90                  95

Ile Thr Leu Val Gly Thr Gln Gly Arg His Ala Gly Gly His Gly Ile
            100                 105                 110

Glu Phe Ala Pro Met Tyr Lys Ile Asn Tyr Ser Arg Asp Gly Thr Arg
        115                 120                 125

Trp Ile Ser Trp Arg Asn Arg His Gly Lys Gln Val Leu Asp Gly Asn
130                 135                 140

Ser Asn Pro Tyr Asp Ile Phe Leu Lys Asp Leu Glu Pro Pro Ile Val
145                 150                 155                 160

Ala Arg Phe Val Arg Phe Ile Pro Val Thr Asp His Ser Met Asn Val
                165                 170                 175

Cys Met Arg Val Glu Leu Tyr Gly Cys Val Trp Leu Asp Gly Leu Val
            180                 185                 190

Ser Tyr Asn Ala Pro Ala Gly Gln Gln Phe Val Leu Pro Gly Gly Ser
        195                 200                 205

Ile Ile Tyr Leu Asn Asp Ser Val Tyr Asp Gly Ala Val Gly Tyr Ser
210                 215                 220

Met Thr Glu Gly Leu Gly Gln Leu Thr Asp Gly Val Ser Gly Leu Asp
225                 230                 235                 240

Asp Phe Thr Gln Thr His Glu Tyr His Val Trp Pro Gly Tyr Asp Tyr
                245                 250                 255

Val Gly Trp Arg Asn Glu Ser Ala Thr Asn Gly Tyr Ile Glu Ile Met
            260                 265                 270

Phe Glu Phe Asp Arg Ile Arg Asn Phe Thr Thr Met Lys Val His Cys
        275                 280                 285

Asn Asn Met Phe Ala Lys Gly Val Lys Ile Phe Lys Glu Val Gln Cys
290                 295                 300

Tyr Phe Arg Ser Glu Ala Ser Glu Trp Glu Pro Asn Ala Ile Ser Phe
305                 310                 315                 320

Pro Leu Val Leu Asp Asp Val Asn Pro Ser Ala Arg Phe Val Thr Val
                325                 330                 335

Pro Leu His His Arg Met Ala Ser Ala Ile Lys Cys Gln Tyr His Phe
            340                 345                 350

Ala Asp Thr Trp Met Met Phe Ser Glu Ile Thr Phe Gln Ser Asp Ala
        355                 360                 365

-continued

```
Ala Met Tyr Asn Asn Ser Glu Ala Leu Pro Thr Ser Pro Met Ala Pro
    370                 375                 380

Thr Thr Tyr Asp Pro Met Leu Lys Val Asp Asp Ser Asn Thr Arg Ile
385                 390                 395                 400

Leu Ile Gly Cys Leu Val Ala Ile Ile Phe Ile Leu Leu Ala Ile Ile
                405                 410                 415

Val Ile Ile Leu Trp Arg Gln Phe Trp Gln Lys Met Leu Glu Lys Ala
            420                 425                 430

Ser Arg Arg Met Leu Asp Asp Glu Met Thr Val Ser Leu Ser Leu Pro
        435                 440                 445

Ser Asp Ser Ser Met Phe Asn Asn Arg Ser Ser Ser Pro Ser Glu
    450                 455                 460

Gln Gly Ser Asn Ser Thr Tyr Asp Arg Ile Phe Pro Leu Arg Pro Asp
465                 470                 475                 480

Tyr Gln Glu Pro Ser Arg Leu Ile Arg Lys Leu Pro Glu Phe Ala Pro
                485                 490                 495

Gly Glu Glu Glu Ser Gly Cys Ser Gly Val Val Lys Pro Val Gln Pro
            500                 505                 510

Ser Gly Pro Glu Gly Val Pro His Tyr Ala Glu Ala Asp Ile Val Asn
        515                 520                 525

Leu Gln Gly Val Thr Gly Gly Asn Thr Tyr Ser Val Pro Ala Val Thr
    530                 535                 540

Met Asp Leu Leu Ser Gly Lys Asp Val Ala Val Glu Glu Phe Pro Arg
545                 550                 555                 560

Lys Leu Leu Thr Phe Lys Glu Lys Leu Gly Glu Gly Gln Phe Gly Glu
                565                 570                 575

Val His Leu Cys Glu Val Glu Gly Met Glu Lys Phe Lys Asp Lys Asp
            580                 585                 590

Phe Ala Leu Asp Val Ser Ala Asn Gln Pro Val Leu Val Ala Val Lys
        595                 600                 605

Met Leu Arg Ala Asp Ala Asn Lys Asn Ala Arg Asn Asp Phe Leu Lys
    610                 615                 620

Glu Ile Lys Ile Met Ser Arg Leu Lys Asp Pro Asn Ile Ile His Leu
625                 630                 635                 640

Leu Ala Val Cys Ile Thr Asp Asp Pro Leu Cys Met Ile Thr Glu Tyr
                645                 650                 655

Met Glu Asn Gly Asp Leu Asn Gln Phe Leu Ser Arg His Glu Pro Pro
            660                 665                 670

Asn Ser Ser Ser Asp Val Arg Thr Val Ser Tyr Thr Asn Leu Lys
        675                 680                 685

Phe Met Ala Thr Gln Ile Ala Ser Gly Met Lys Tyr Leu Ser Ser Leu
    690                 695                 700

Asn Phe Val His Arg Asp Leu Ala Thr Arg Asn Cys Leu Val Gly Lys
705                 710                 715                 720

Asn Tyr Thr Ile Lys Ile Ala Asp Phe Gly Met Ser Arg Asn Leu Tyr
                725                 730                 735

Ser Gly Asp Tyr Tyr Arg Ile Gln Gly Arg Ala Val Leu Pro Ile Arg
            740                 745                 750

Trp Met Ser Trp Glu Ser Ile Leu Leu Gly Lys Phe Thr Thr Ala Ser
        755                 760                 765

Asp Val Trp Ala Phe Gly Val Thr Leu Trp Glu Thr Phe Thr Phe Cys
    770                 775                 780

Gln Glu Gln Pro Tyr Ser Gln Leu Ser Asp Glu Gln Val Ile Glu Asn
```

```
                    785                 790                 795                 800
Thr Gly Glu Phe Phe Arg Asp Gln Gly Arg Gln Thr Tyr Leu Pro Gln
                    805                 810                 815

Pro Ala Ile Cys Pro Asp Ser Val Tyr Lys Leu Met Leu Ser Cys Trp
                820                 825                 830

Arg Arg Asp Thr Lys Asn Arg Pro Ser Phe Gln Glu Ile His Leu Leu
            835                 840                 845

Leu Leu Gln Gln Gly Asp Glu
        850                 855

<210> SEQ ID NO 2
<211> LENGTH: 58
<212> TYPE: DNA
<213> ORGANISM: Artificial Sequence
<220> FEATURE:
<223> OTHER INFORMATION: laboratory synthesized primer

<400> SEQUENCE: 2
ccggcccatg cctatgccac tccatctcga gatggagtgg cataggcatg ggttttttg      58

<210> SEQ ID NO 3
<211> LENGTH: 58
<212> TYPE: DNA
<213> ORGANISM: Artificial Sequence
<220> FEATURE:
<223> OTHER INFORMATION: laboratory synthesized primer

<400> SEQUENCE: 3
ccggccctgg aggttccatc atttactcga gtaaatgatg gaacctccag ggttttttg      58

<210> SEQ ID NO 4
<211> LENGTH: 211
<212> TYPE: PRT
<213> ORGANISM: Homo sapiens
<220> FEATURE:
<221> NAME/KEY: VARIANT
<222> LOCATION: (1)...(211)
<223> OTHER INFORMATION: NCBI Reference Sequence: NP_001014796.1
      residues 54-264

<400> SEQUENCE: 4

Glu Ser Thr Ala Ala Lys Tyr Gly Arg Leu Asp Ser Glu Glu Gly Asp
 1               5                  10                  15

Gly Ala Trp Cys Pro Glu Ile Pro Val Glu Pro Asp Asp Leu Lys Glu
                20                  25                  30

Phe Leu Gln Ile Asp Leu His Thr Leu His Phe Ile Thr Leu Val Gly
            35                  40                  45

Thr Gln Gly Arg His Ala Gly Gly His Gly Ile Glu Phe Ala Pro Met
        50                  55                  60

Tyr Lys Ile Asn Tyr Ser Arg Asp Gly Thr Arg Trp Ile Ser Trp Arg
65                  70                  75                  80

Asn Arg His Gly Lys Gln Val Leu Asp Gly Asn Ser Asn Pro Tyr Asp
                85                  90                  95

Ile Phe Leu Lys Asp Leu Glu Pro Pro Ile Val Ala Arg Phe Val Arg
                100                 105                 110

Phe Ile Pro Val Thr Asp His Ser Met Asn Val Cys Met Arg Val Glu
            115                 120                 125

Leu Tyr Gly Cys Val Trp Leu Asp Gly Leu Val Ser Tyr Asn Ala Pro
        130                 135                 140

Ala Gly Gln Gln Phe Val Leu Pro Gly Gly Ser Ile Ile Tyr Leu Asn
```

```
145                 150                 155                 160
Asp Ser Val Tyr Asp Gly Ala Val Gly Tyr Ser Met Thr Glu Gly Leu
                165                 170                 175

Gly Gln Leu Thr Asp Gly Val Ser Gly Leu Asp Asp Phe Thr Gln Thr
                180                 185                 190

His Glu Tyr His Val Trp Pro Gly Tyr Asp Tyr Val Gly Trp Arg Asn
                195                 200                 205

Glu Ser Ala
    210

<210> SEQ ID NO 5
<211> LENGTH: 320
<212> TYPE: PRT
<213> ORGANISM: Homo sapiens
<220> FEATURE:
<221> NAME/KEY: VARIANT
<222> LOCATION: (1)...(320)
<223> OTHER INFORMATION: NCBI Reference Sequence: NP_001014796.1
      residues 468-787

<400> SEQUENCE: 5

Asn Ser Thr Tyr Asp Arg Ile Phe Pro Leu Arg Pro Asp Tyr Gln Glu
  1               5                  10                  15

Pro Ser Arg Leu Ile Arg Lys Leu Pro Glu Phe Ala Pro Gly Glu Glu
                 20                  25                  30

Glu Ser Gly Cys Ser Gly Val Val Lys Pro Val Gln Pro Ser Gly Pro
             35                  40                  45

Glu Gly Val Pro His Tyr Ala Glu Ala Asp Ile Val Asn Leu Gln Gly
         50                  55                  60

Val Thr Gly Gly Asn Thr Tyr Ser Val Pro Ala Val Thr Met Asp Leu
 65                  70                  75                  80

Leu Ser Gly Lys Asp Val Ala Val Glu Glu Phe Pro Arg Lys Leu Leu
                 85                  90                  95

Thr Phe Lys Glu Lys Leu Gly Glu Gly Gln Phe Gly Glu Val His Leu
                100                 105                 110

Cys Glu Val Glu Gly Met Glu Lys Phe Lys Asp Lys Asp Phe Ala Leu
            115                 120                 125

Asp Val Ser Ala Asn Gln Pro Val Leu Val Ala Val Lys Met Leu Arg
        130                 135                 140

Ala Asp Ala Asn Lys Asn Ala Arg Asn Asp Phe Leu Lys Glu Ile Lys
145                 150                 155                 160

Ile Met Ser Arg Leu Lys Asp Pro Asn Ile Ile His Leu Leu Ala Val
                165                 170                 175

Cys Ile Thr Asp Asp Pro Leu Cys Met Ile Thr Glu Tyr Met Glu Asn
                180                 185                 190

Gly Asp Leu Asn Gln Phe Leu Ser Arg His Glu Pro Pro Asn Ser Ser
            195                 200                 205

Ser Ser Asp Val Arg Thr Val Ser Tyr Thr Asn Leu Lys Phe Met Ala
        210                 215                 220

Thr Gln Ile Ala Ser Gly Met Lys Tyr Leu Ser Ser Leu Asn Phe Val
225                 230                 235                 240

His Arg Asp Leu Ala Thr Arg Asn Cys Leu Val Gly Lys Asn Tyr Thr
                245                 250                 255

Ile Lys Ile Ala Asp Phe Gly Met Ser Arg Asn Leu Tyr Ser Gly Asp
                260                 265                 270

Tyr Tyr Arg Ile Gln Gly Arg Ala Val Leu Pro Ile Arg Trp Met Ser
```

```
              275                 280                 285
Trp Glu Ser Ile Leu Leu Gly Lys Phe Thr Thr Ala Ser Asp Val Trp
    290                 295                 300
Ala Phe Gly Val Thr Leu Trp Glu Thr Phe Thr Phe Cys Gln Glu Gln
305                 310                 315                 320

<210> SEQ ID NO 6
<211> LENGTH: 211
<212> TYPE: PRT
<213> ORGANISM: Mus musculus
<220> FEATURE:
<221> NAME/KEY: VARIANT
<222> LOCATION: (1)...(211)
<223> OTHER INFORMATION: NP_072075.2 residues 54-264

<400> SEQUENCE: 6

Glu Ser Thr Ala Ala Lys Tyr Gly Arg Leu Asp Ser Glu Glu Gly Asp
  1               5                  10                  15
Gly Ala Trp Cys Pro Glu Ile Pro Val Gln Pro Asp Asp Leu Lys Glu
             20                  25                  30
Phe Leu Gln Ile Asp Leu Arg Thr Leu His Phe Ile Thr Leu Val Gly
         35                  40                  45
Thr Gln Gly Arg His Ala Gly Gly His Gly Ile Glu Phe Ala Pro Met
     50                  55                  60
Tyr Lys Ile Asn Tyr Ser Arg Asp Gly Thr Arg Trp Ile Ser Trp Arg
 65                  70                  75                  80
Asn Arg His Gly Lys Gln Val Leu Asp Gly Asn Ser Asn Pro Tyr Asp
                 85                  90                  95
Val Phe Leu Lys Asp Leu Glu Pro Pro Ile Val Ala Arg Phe Val Arg
            100                 105                 110
Leu Ile Pro Val Thr Asp His Ser Met Asn Val Cys Met Arg Val Glu
        115                 120                 125
Leu Tyr Gly Cys Val Trp Leu Asp Gly Leu Val Ser Tyr Asn Ala Pro
    130                 135                 140
Ala Gly Gln Gln Phe Val Leu Pro Gly Gly Ser Ile Ile Tyr Leu Asn
145                 150                 155                 160
Asp Ser Val Tyr Asp Gly Ala Val Gly Tyr Ser Met Thr Glu Gly Leu
                165                 170                 175
Gly Gln Leu Thr Asp Gly Val Ser Gly Leu Asp Asp Phe Thr Gln Thr
            180                 185                 190
His Glu Tyr His Val Trp Pro Gly Tyr Asp Tyr Val Gly Trp Arg Asn
        195                 200                 205
Glu Ser Ala
    210

<210> SEQ ID NO 7
<211> LENGTH: 319
<212> TYPE: PRT
<213> ORGANISM: Mus musculus
<220> FEATURE:
<221> NAME/KEY: VARIANT
<222> LOCATION: (1)...(319)
<223> OTHER INFORMATION: NP_072075.2 residues 468-786

<400> SEQUENCE: 7

Asn Ser Thr Tyr Asp Arg Ile Phe Pro Leu Arg Pro Asp Tyr Gln Glu
  1               5                  10                  15
Pro Ser Arg Leu Ile Arg Lys Leu Pro Glu Phe Ala Pro Gly Glu Glu
             20                  25                  30
```

-continued

```
Glu Ser Gly Cys Ser Gly Val Lys Pro Ala Gln Pro Asn Gly Pro
            35                  40                  45

Glu Gly Val Pro His Tyr Ala Glu Ala Asp Ile Val Asn Leu Gln Gly
         50                  55                  60

Val Thr Gly Gly Asn Thr Tyr Cys Val Pro Ala Val Thr Met Asp Leu
 65                  70                  75                  80

Leu Ser Gly Lys Asp Val Ala Val Glu Glu Phe Pro Arg Lys Leu Leu
                 85                  90                  95

Ala Phe Lys Glu Lys Leu Gly Glu Gly Gln Phe Gly Glu Val His Leu
            100                 105                 110

Cys Glu Val Glu Gly Met Glu Lys Phe Lys Asp Lys Asp Phe Ala Leu
        115                 120                 125

Asp Val Ser Ala Asn Gln Pro Val Leu Val Ala Val Lys Met Leu Arg
    130                 135                 140

Ala Asp Ala Asn Lys Asn Ala Arg Asn Asp Phe Leu Lys Glu Ile Lys
145                 150                 155                 160

Ile Met Ser Arg Leu Lys Asp Pro Asn Ile Ile Arg Leu Leu Ala Val
                165                 170                 175

Cys Ile Thr Glu Asp Pro Leu Cys Met Ile Thr Glu Tyr Met Glu Asn
            180                 185                 190

Gly Asp Leu Asn Gln Phe Leu Ser Arg His Glu Pro Leu Ser Ser Cys
        195                 200                 205

Ser Ser Asp Ala Thr Val Ser Tyr Ala Asn Leu Lys Phe Met Ala Thr
    210                 215                 220

Gln Ile Ala Ser Gly Met Lys Tyr Leu Ser Ser Leu Asn Phe Val His
225                 230                 235                 240

Arg Asp Leu Ala Thr Arg Asn Cys Leu Val Gly Lys Asn Tyr Thr Ile
                245                 250                 255

Lys Ile Ala Asp Phe Gly Met Ser Arg Asn Leu Tyr Ser Gly Asp Tyr
            260                 265                 270

Tyr Arg Ile Gln Gly Arg Ala Val Leu Pro Ile Arg Trp Met Ser Trp
        275                 280                 285

Glu Ser Ile Leu Leu Gly Lys Phe Thr Thr Ala Ser Asp Val Trp Ala
    290                 295                 300

Phe Gly Val Thr Leu Trp Glu Thr Phe Thr Phe Cys Gln Glu Gln
305                 310                 315

<210> SEQ ID NO 8
<211> LENGTH: 210
<212> TYPE: PRT
<213> ORGANISM: Danio rerio
<220> FEATURE:
<221> NAME/KEY: VARIANT
<222> LOCATION: (1)...(210)
<223> OTHER INFORMATION: NCBI Reference Sequence: XP_687859.4 residues
      27-236

<400> SEQUENCE: 8

Glu Ser Thr Ala Ala Arg Tyr Gly Arg Leu Asp Phe Asp Asp Gly Asp
  1               5                  10                  15

Gly Ala Trp Cys Pro Asp Val Met Ala Glu Ala His Ser Leu Lys Glu
             20                  25                  30

Phe Leu Gln Ile Asp Leu Arg Thr Leu His Phe Val Thr Leu Val Gly
         35                  40                  45

Thr Gln Gly Arg His Ala Asp Gly Val Gly Asn Glu Phe Ala Gln Arg
     50                  55                  60
```

```
Tyr Arg Ile Lys Tyr Ser Arg Asp Gly Thr Arg Trp Val Ser Trp Arg
 65                  70                  75                  80

Asp Arg Gln Gly Arg Gln Ile Ile Glu Gly Asn Ser Asn Ala Tyr Asp
                 85                  90                  95

Ile Val Leu Lys Asp Leu Glu Pro Ile Ile Ala Arg Phe Val Arg
            100                 105                 110

Phe Met Pro Val Thr Asp Pro Ser Met Ile Val Cys Met Arg Val Glu
            115                 120                 125

Leu Tyr Gly Cys Glu Trp Leu Asp Gly Leu Val Ser Tyr Ser Ala Pro
            130                 135                 140

Ala Gly Gln Gln Met Thr Phe Arg Gly Gln Gln Ile Tyr Leu Asn Asp
145                 150                 155                 160

Thr Val Tyr Asp Gly Ala Val Ser Ser Ser Met Ala Glu Gly Leu Gly
                165                 170                 175

Gln Leu Thr Asp Gly Ser Trp Gly Leu Asp Asp Phe Thr Lys Ser Gln
            180                 185                 190

Val Tyr Gly Val Trp Pro Gly Tyr Asp Tyr Val Gly Trp Thr Asn Ala
            195                 200                 205

Ser Leu
    210

<210> SEQ ID NO 9
<211> LENGTH: 313
<212> TYPE: PRT
<213> ORGANISM: Danio rerio
<220> FEATURE:
<221> NAME/KEY: VARIANT
<222> LOCATION: (1)...(313)
<223> OTHER INFORMATION: NCBI Reference Sequence: XP_687859.4 residues
      443-755

<400> SEQUENCE: 9

Thr Ser Thr Tyr Glu Arg Ile Phe Pro Leu Gly Ser Asp Tyr Gln Glu
  1               5                  10                  15

Pro Ser Gln Leu Leu Arg Lys Leu Pro Glu Phe Gln Ala Met Glu Asn
                 20                  25                  30

Leu Ala Met Ile Asp Gly Ala Ser Glu Pro Ser Pro Ala Gln Gly Thr
             35                  40                  45

Asp Glu Ala Pro His Tyr Ala Glu Ala Asp Ile Pro Gly Ala His Ser
         50                  55                  60

Tyr Arg Val Thr Val Val Asn Met Pro Leu Ser Pro Gly Arg Asp Gly
 65                  70                  75                  80

Ala Leu Glu Glu Phe Pro Arg Asp Arg Leu Thr Phe Lys Glu Lys Leu
                 85                  90                  95

Gly Glu Gly Gln Phe Gly Glu Val His Leu Cys Glu Ala Glu Gly Met
            100                 105                 110

Gln Glu Phe Met Lys Asp His Cys Asp Asp Ile Cys Val Asp Pro Met
            115                 120                 125

Leu Val Ala Val Lys Thr Leu Arg Glu Asp Ala Asp Lys Asn Ala Arg
            130                 135                 140

Asn Asp Phe Met Lys Glu Ile Arg Ile Ile Ser Arg Leu Arg Asp Pro
145                 150                 155                 160

Asn Ile Ile Arg Leu Leu Ala Val Cys Val Glu Ser Asp Pro Leu Cys
                165                 170                 175

Met Ile Thr Glu Tyr Met Glu Asn Gly Asp Leu Asn Gln Phe Leu Ser
            180                 185                 190
```

```
Arg His Gln Leu Gln Glu Asp Gly Val Gln Ala Asp Ser Thr Ser Ile
        195                 200                 205

Ser Tyr Gly Thr Leu Ile Asn Met Ala Ser Gln Ile Ser Ser Gly Met
210                 215                 220

Lys Tyr Leu Ser Ser Leu Asn Phe Val His Arg Asp Leu Ala Thr Arg
225                 230                 235                 240

Asn Cys Leu Val Gly Met Asn Asn Ile Ile Lys Ile Ala Asp Phe Gly
                245                 250                 255

Met Ser Arg Asn Leu Tyr Arg Gly Asp Tyr Tyr Arg Ile Gln Gly Arg
            260                 265                 270

Ala Val Leu Pro Ile Arg Trp Met Ser Trp Glu Ser Ile Leu Leu Gly
        275                 280                 285

Lys Phe Thr Met Ala Ser Asp Val Trp Ala Phe Gly Val Thr Leu Trp
290                 295                 300

Glu Ile Leu Thr Leu Cys Lys Glu Gln
305                 310
```

<210> SEQ ID NO 10
<211> LENGTH: 199
<212> TYPE: PRT
<213> ORGANISM: Caenorhabditis elegans
<220> FEATURE:
<221> NAME/KEY: VARIANT
<222> LOCATION: (1)...(199)
<223> OTHER INFORMATION: UniProtKB/Swiss-Prot: Q95ZV7 residues 50-248

<400> SEQUENCE: 10

```
Gln Ser Thr Gly Pro Gln His Ala Arg Ala His Gln Glu Ser Gly Ser
  1               5                  10                  15

Gly Ala Trp Cys Pro Lys Asn Gln Ile Asn Ser Leu Ser Lys Glu Trp
             20                  25                  30

Leu Gln Ile Ser Phe Ser Val Asp Thr Val Ile Thr Ser Val Glu Thr
         35                  40                  45

Gln Gly Arg Phe Asp Asp Gly Arg Gly Met Glu Tyr Ala Thr Ala Phe
     50                  55                  60

Lys Ile Gln Tyr Trp Arg Pro Ser Leu Asn Ala Trp Ala Ser Tyr Lys
 65                  70                  75                  80

Asp Asp Phe Glu Leu Glu Thr Ile Pro Ala Asn Asn Asp Thr Glu His
                 85                  90                  95

Ala Ile Arg Arg His Leu Asp Arg Ala Ile Ile Ala Arg Arg Ile Arg
            100                 105                 110

Ile Val Pro Val Ser Asn Ser Thr Arg Thr Val Cys Met Arg Val Glu
        115                 120                 125

Val Phe Gly Cys Pro Phe Asp Asp Ser Leu Val Phe Tyr Asn Val Asp
130                 135                 140

Gln Gly Asp Leu Gln Ser Gly Ile Ser Tyr His Asp Phe Ser Tyr Asp
145                 150                 155                 160

Gly Asn Leu Ala Asn Ser Pro His Leu Thr Gly Gly Ile Gly Lys Leu
                165                 170                 175

Tyr Asp Gly Glu Val Gly Lys Asn Asn Val Phe Val Asn His His Lys
            180                 185                 190

Trp Val Gly Trp Arg Arg Lys
        195
```

<210> SEQ ID NO 11
<211> LENGTH: 272

-continued

```
<212> TYPE: PRT
<213> ORGANISM: Caenorhabditis elegans
<220> FEATURE:
<221> NAME/KEY: VARIANT
<222> LOCATION: (1)...(272)
<223> OTHER INFORMATION: UniProtKB/Swiss-Prot: Q95ZV7 residues 451-722

<400> SEQUENCE: 11

Leu Gln Asn Ala Leu Ile Glu Lys Met Pro Met Ser Pro Ile Ile Ser
 1               5                  10                  15

Asp Tyr Ala Glu Pro Asp Ile Ser Val Cys Ser Asp Val Thr Ala Asn
            20                  25                  30

Thr Pro Leu Leu Tyr Gly Ile Asp Gly Pro Tyr Asp Thr Gln Lys Arg
        35                  40                  45

Ser Asn Pro Leu Ser Ser Met Val Lys Tyr Ser Asp Tyr Gly Glu Val
    50                  55                  60

Tyr Cys Thr Thr Leu Pro Glu Ile Ala Arg Asp Lys Leu Ile Cys Val
65                  70                  75                  80

Ser Arg Ile Gly Gln Gly Glu Phe Gly Glu Val Asp Leu Cys Gln Leu
                85                  90                  95

Glu Asn Arg Lys Val Ala Val Lys Lys Leu His Gly Ile Ser Gln Ala
            100                 105                 110

Asp Glu Phe Ser Phe His Arg Glu Ile Arg Val Leu Gly Ser Leu Lys
        115                 120                 125

His Pro Asn Val Val Glu Val Val Gly Val Cys Thr Ile Gln Lys Pro
    130                 135                 140

Ile Leu Cys Ile Met Glu Tyr Met Glu Asn Gly Asp Leu Lys Ser Tyr
145                 150                 155                 160

Ile Leu Lys Asn Pro Thr Ile Gln Thr Ser Gln Cys Ile Ser Ile Cys
                165                 170                 175

Thr Gln Leu Ala Ala Gly Leu Ala Tyr Leu Glu Ser Cys Asn Phe Val
            180                 185                 190

His Arg Asp Ile Ala Ala Arg Asn Cys Leu Val Asp Gly Glu Gly Asn
        195                 200                 205

Val Lys Ile Ala Asp Phe Gly Met Ala Arg Ser Leu Tyr Ser Gln Glu
    210                 215                 220

Tyr Tyr Lys Val Glu Gly Lys Phe Val Leu Pro Ile Arg Trp Met Ala
225                 230                 235                 240

Trp Glu Ala Leu Leu Leu Gly Lys Phe Ser Thr Ala Ser Asp Val Trp
                245                 250                 255

Gly Phe Gly Val Thr Met Trp Glu Ile Phe Ser Leu Cys Ser Glu Lys
            260                 265                 270
```

DDR2 MUTATIONS IN SQUAMOUS CELL LUNG CANCER

CLAIM OF PRIORITY

This application is a continuation under 35 USC 111 of International Patent Application No. PCT/US2013/030292, filed on Mar. 11, 2013, and claims the benefit of U.S. Provisional Patent Application Ser. No. 61/619,273, filed on Apr. 2, 2012. The entire contents of the foregoing are hereby incorporated by reference.

FEDERALLY SPONSORED RESEARCH OR DEVELOPMENT

This invention was made with Government support under Grant No. LC090577 awarded by the Department of Defense and Grant No. T32CA09172 awarded by the National Institutes of Health. The Government has certain rights in the invention.

TECHNICAL FIELD

This invention relates to methods for treating patients with squamous cell lung cancer, including detecting the presence of mutations in the discoidin domain receptor 2 (DDR2) gene.

BACKGROUND

Lung cancer is the leading cause of cancer-related mortality in the United States with over 157,000 deaths projected in 2010 (1). The more common type of lung cancer, non-small cell lung cancer (NSCLC), accounts for 85% of cases and carries a grim prognosis with approximately 70% of patients presenting with advanced and often incurable disease at the time of diagnosis (2).

Despite these statistics a great deal of progress has been made in the targeted treatment of patients with NSCLC, largely due to the development of small molecule inhibitors of the epidermal growth factor receptor (EGFR) tyrosine kinase (3-5). Patients who respond to EGFR kinase inhibitors are much more likely to have the adenocarcinoma subtype of NSCLC (6). Patients with the other principal subtype of NSCLC, lung squamous cell cancer (lung SCC), very rarely respond to these agents and few advances have been made in the treatment of this type of lung cancer which comprises 25% of NSCLC. In addition to EGFR, several other promising therapeutic targets have been identified in the laboratory such as EML4-ALK, KRAS and MET; drugs directed against these proteins are being tested in clinical trials (7-10). However, it appears that these targets are likely limited to adenocarcinomas as well. A recent report has suggested that targeting FGFR1 amplifications in SCC of the lung may be a promising therapeutic strategy, though FGFR inhibitors are not currently in clinical use for the treatment of patients with lung cancer (11).

SUMMARY

At least in part, the present invention is based on the discovery that mutations in the DDR2 kinase gene identify a novel therapeutic target in squamous cell lung cancer, and can be used to select therapy for patients whose tumors comprises cells harboring DDR2 mutations, e.g., administration of tyrosine kinase inhibitors such as dasatinib.

Thus in a first aspect, the invention provides methods for selecting a treatment comprising administration of a tyrosine kinase inhibitor (TKI) for a subject diagnosed with lung cancer, e.g., non-small cell lung cancer (NSCLC), e.g., squamous cell carcinoma (SCC). The methods include determining a nucleic acid sequence of all or part of a discoidin domain receptor 2 (DDR2) gene in a sample comprising nucleated cells from the SCC in the subject; determining an expected amino acid translation of the determined DDR2 sequence; and comparing the expected amino acid translation with a reference amino acid sequence, wherein the reference amino acid sequence is a wild type DDR2 sequence; detecting the presence of at least one amino acid variation relative to the reference amino acid sequence; and selecting a treatment comprising administration of a TKI for the subject, based on the presence of at least one amino acid variation relative to the reference sequence.

In a further aspect, the invention provides methods for predicting response to a treatment comprising administration of a tyrosine kinase inhibitor (TKI) in a subject diagnosed with squamous cell carcinoma (SCC). The methods include determining a nucleic acid sequence of all or part of a discoidin domain receptor 2 (DDR2) gene in a sample comprising nucleated cells from the SCC in the subject; determining an expected amino acid translation of the determined DDR2 sequence; and comparing the expected amino acid translation with a reference amino acid sequence, wherein the reference amino acid sequence is a wild type DDR2 sequence; detecting the presence of at least one amino acid variation relative to the reference amino acid sequence; and selecting a treatment comprising administration of a TKI for the subject, based on the presence of the at least one amino acid variation relative to the reference sequence.

In some embodiments of the methods described herein, the subject is human and the reference amino acid sequence comprises SEQ ID NO:1. In some embodiments of the methods described herein, the reference sequence is obtained from non-cancerous cells of the same subject.

In some embodiments of the methods described herein, the at least one amino acid variation comprises a non-conservative amino acid substitution.

In some embodiments of the methods described herein, the at least one amino acid variation is within a kinase domain (amino acids 563-849) or discoidin domain (amino acids 30-185) of DDR2.

In some embodiments of the methods described herein, the at least one amino acid variation is L63V, I120M, D125Y, L239R, G253C, G505S, C580Y, I638F, T765P, G774E/V, or S768R. In some embodiments of the methods described herein, the variation is due to a mutation is shown in Tables 7 or 8.

In some embodiments of the methods described herein, the methods include determining a nucleic acid sequence of a coding region of a discoidin domain receptor 2 (DDR2) gene.

In some embodiments of the methods described herein, the at least one amino acid variation results in a decrease in expression levels, half-life, or kinase activity of the DDR2 protein.

In some embodiments of the methods described herein, the TKI is dasatinib, nilotinib, imatinib, or ponatinib. In some embodiments of the methods described herein, the TKI is dasatinib.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1a-c: Sequencing of squamous lung cancer samples identifies recurrent mutations in DDR2. (a) Schema depicted for the primary, secondary and validation screens for DDR2 mutations in squamous lung cancer samples. (b) Amino acid sequence of DDR2 with the positions of the identified mutations shown in the context of the known domain structure of DDR2. (c) Homology alignment of DDR2 amino acid sequence. Shown are the amino acid sequences of human DDR2, listed as DDR2 HUMAN residues 54-264 (SEQ ID NO:4) and 468-787 (SEQ ID NO:5); mouse DDR2, listed as DDR2 MOUSE residues 54-264 (SEQ ID NO:6) and 468-786 (SEQ ID NO:7); and the closest homologs in zebrafish, shown as ASWUM4_DANRE residues 27-236 (SEQ ID NO:8) and 443-755 (SEQ ID NO:9) and *C. elegans*, shown as Q95ZV7_CAEEL residues 50-248 (SEQ ID NO:10) and 451-722 (SEQ ID NO:11). Degree of homology is indicated by the bar graphs under each amino acid and the position of the novel DDR2 mutations indicated.

DETAILED DESCRIPTION

Figure 1A:
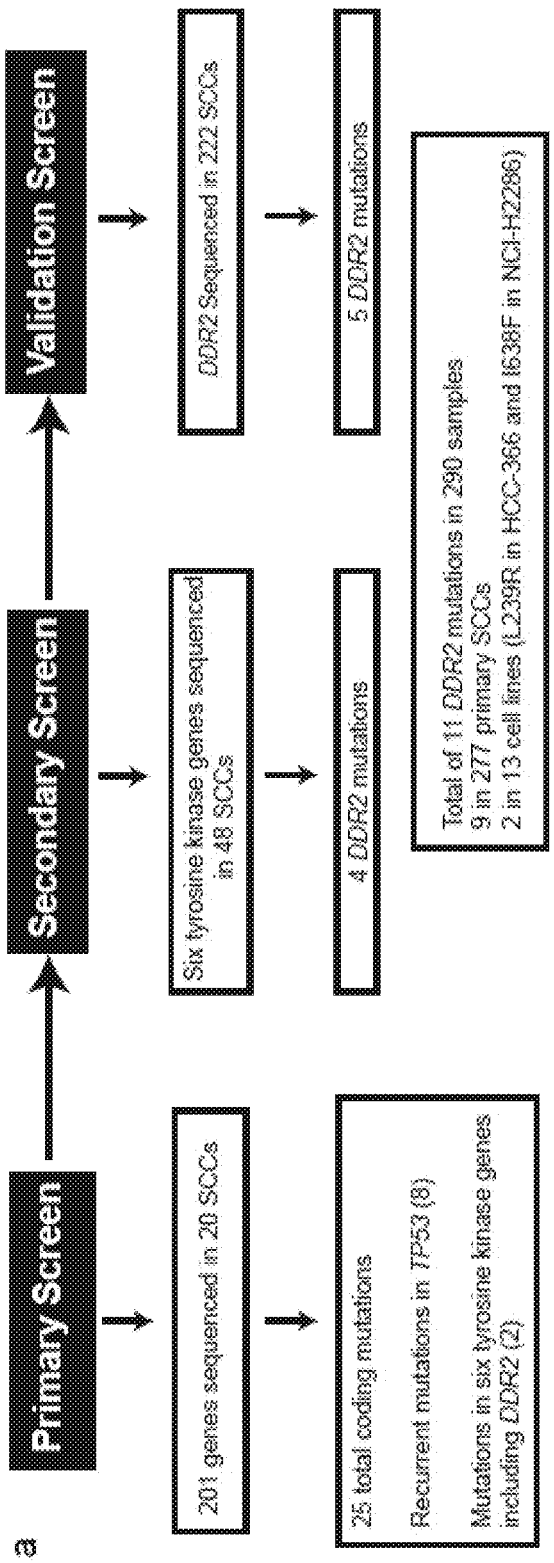

Described herein is the identification of novel somatic mutations in the discoidin domain receptor 2 (DDR2) tyrosine kinase gene at a frequency of 3.8% (n=11) in a sample set of 290 squamous cell lung cancer samples. DDR2 is a receptor tyrosine kinase which binds collagen as its endogenous ligand and has been previously shown to promote cell migration, proliferation and survival when activated by ligand binding and phosphorylation (12-18). DDR1 and DDR2 mutations have been reported in several cancer specimens, including four DDR1 mutations (W385C, A496S, F866Y, F824W) and two DDR2 mutations in lung cancer (R105S and N456S), but these reports have not been confirmed in independent samples and functional characterization of the mutations has not been reported (19-21). As demonstrated herein, DDR2 mutation status is associated with sensitivity to the tyrosine kinase inhibitor dasatinib or to sh-RNA mediated depletion of DDR2. Additionally, DDR2 mutations are oncogenic and their ability to transform cells can be blocked by dasatinib treatment or by combination tyrosine kinase inhibitor treatment. Furthermore, a DDR2 kinase domain mutation was observed in a clinical trial subject with SCC of the lung who had a radiographic response to combination therapy with erlotinib and dasatinib and who did not have an EGFR mutation. Together, these data indicate that DDR2 may be an important therapeutic target in SCCs, and can be used to select therapy for patients with SCC.

DEFINITIONS

As used herein, an "allele" is one of a pair or series of genetic variants at a specific genomic location. A "response allele" is an allele that is associated with increased likelihood of response; heterozygosity is sufficient as these are gain-of-function. Where a SNP is biallelic, one allele (the "response allele") will be associated with increased likelihood of response, while the other allele is associated with average or decreased likelihood of response, or some variation thereof.

As used herein, "genotype" refers to the diploid combination of alleles for a given genetic polymorphism. A homozygous subject carries two copies of the same allele and a heterozygous subject carries two different alleles.

Microsatellites (sometimes referred to as a variable number of tandem repeats or VNTRs) are short segments of DNA that have a repeated sequence, usually about 2 to 5 nucleotides long (e.g., CACACA), that tend to occur in non-coding DNA. Changes in the microsatellites sometimes occur during the genetic recombination of sexual reproduction, increasing or decreasing the number of repeats found at an allele, changing the length of the allele. Microsatellite markers are stable, polymorphic, easily analyzed and occur regularly throughout the genome, making them especially suitable for genetic analysis.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs.

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "reference sequence" refers to a sequence that is present in a subject considered to be a reference or control subject. The reference sequence as used in some embodiments is a sequence that is present in the majority of a population, i.e., the "wild-type" sequence. In some embodiments, the reference sequence is nucleic acid (e.g., genomic DNA or mRNA/cDNA) or amino acid. In some embodiments, the reference sequence is a sequence in the same subject at an earlier time point, e.g., before treatment. In some embodiments, the reference sequence is obtained from non-cancerous cells of the same subject.

The term "probe" refers to an oligonucleotide. In some embodiments, a probe is single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and non-isotopic labels, such as enzymes, biotin, avidin, streptavidin, digoxygenin, luminescent agents, dyes, haptens, and the like. Luminescent agents, depending upon the source of exciting energy, can be classified as radio luminescent, chemiluminescent, bioluminescent, and photoluminescent (including fluorescent and phosphorescent). In some embodiments, a probe described herein is bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. In some embodiments, targets for hybridization are derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences are performed using methods known in the art, e.g., as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30% (e.g., at least 30%, 40%, 50%, 60%, 70%, 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

In some embodiments, the comparison of sequences and determination of percent identity between two sequences is accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80% (e.g., 85%, 90%, 95%, 97% or more) identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

Methods of Selecting Treatment

Described herein are a number of methods of selecting a treatment comprising administration of a tyrosine kinase inhibitor for a subject who has squamous cell lung cancer.

As used herein, "detecting a variant DDR2" includes obtaining information regarding the identity (i.e., of a specific nucleotide), presence or absence of one or more specific sequences or alleles in a subject. Detecting a variant DDR2 can, but need not, include obtaining a sample comprising DNA from a subject, e.g., from an SCC tumor cell, and/or assessing the identity, presence or absence of a specific sequence or one or more genetic markers in the sample. The individual or organization who detects the variant DDR2 need not actually carry out the physical analysis of a sample from a subject; the methods can include using information obtained by analysis of the sample by a third party. Thus the methods can include steps that occur at more than one site. In some embodiments, a sample is obtained from a subject at a first site, such as at a health care provider. In some embodiments, the sample is analyzed at the same or a second site, e.g., at a laboratory or other testing facility.

In some embodiments, to detect a variant DDR2, a biological sample that includes nucleated cells (such as blood, a cheek swab or mouthwash) is prepared and analyzed for sequence or the presence or absence of pre-selected markers. Such diagnoses may be performed by diagnostic laboratories, or, alternatively, in some embodiments, diagnostic kits are manufactured and sold to health care providers or to private individuals for self-diagnosis. In some embodiments, diagnostic or prognostic tests are performed as described herein or using well known techniques, such as described in U.S. Pat. No. 5,800,998.

In some embodiments, results of these tests, and optionally interpretive information, are returned to the subject, the health care provider or to a third party payor. The results can be used in a number of ways. In some embodiments, the information is communicated to the tested subject, e.g., with a prognosis and optionally interpretive materials that help the subject understand the test results and prognosis. In some embodiments, the information is used, e.g., by a health care provider, to determine whether to administer a treatment comprising a TKI for SCC, or whether a subject should be assigned to a specific category, e.g., a category associated with a specific disease, or with drug response or non-response. In some embodiments, the information is used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments comprising administration of a TKI for SCC if the subject has a variant of DDR2 and this is likely to response to a TKI. The presence or absence of a DDR2 variant, e.g., as described herein, in a subject may be ascertained by using any of the methods described herein.

The methods can include obtaining a sample comprising cells from the subject, e.g., cells from a SCC tumor biopsy, and determining the sequence of all or part of the DDR2 gene. In some embodiments, genomic DNA is sequenced; in some embodiments, mRNA is sequenced (optionally after conversion to cDNA). In some embodiments, rather than sequencing all or part of a gene, the identity of a single nucleotide is determined.

Squamous Cell Lung Cancer

Non-small-cell lung cancer (NSCLC) is the leading cause of cancer mortality in the United States and worldwide (Higgins and Ettinger, Expert Rev Anticancer Ther 2009; 9:1365-1378). Non-small-cell lung cancer can be divided into three major histological subtypes: squamous cell carcinoma, adenocarcinoma (AC) and large cell carcinoma (LCC). The vast majority of SCCs arise in subsegmental or larger bronchi and grow centrally toward the main bronchus, infiltrating the underlying bronchial cartilage, lymph nodes, and adjacent lung parenchyma. The other types of NSCLC (AC and LCC) are often peripherally located in the lungs. Although exemplified in SCC, the methods described herein could be used in the other types of lung cancer, e.g., SCLC and NSCLC.

A suspected case of lung cancer, e.g., SCC can be initially identified based on symptoms, followed by the presence of findings consistent with lung cancer, e.g., SCC on imaging studies, e.g., chest radiographs, Magnetic Resonance Imaging (MRI), positron emission tomography (PET), or computed tomography (CT), and a confirmed diagnosis obtained by histology, e.g., by sputum cytologic studies, bronchoscopy, or CT-guided transthoracic needle biopsy of the mass; selection of the method can depend on the location of the tumor.

DDR2

DDR2 is a receptor tyrosine kinase that activates intracellular signaling pathways including Ras/MAPK, ERK and NF-kB upon stimulation by its endogenous ligand, extracellular collagen (Vogel et al., J Biol Chem, 2000. 275(8): 5779-84; Vogel et al., Mol Cell, 1997. 1(1):13-23; Vogel et al., Mol Cell Biol, 2001. 21(8):2906-17). DDR2 is thought to be important in regulating cell growth and survival, as a DDR2 null mouse exhibits dwarfism and infertility and a family of humans with germline hypomophic DDR2 mutations have short limbs and a short stature (Bargal et al., Am J Hum Genet, 2009. 84(1): 80-4). DDR2 mutations have been described as rare events in a variety of cancers including a single report in lung cancer, though the significance of these events is unknown. (Rikova et al., Cell, 2007. 131(6): 1190-203; Tomasson et al., Blood, 2008. 111(9):4797-808) Furthermore, DDR2 has been identified as a target of the FDA-approved tyrosine kinase inhibitors imatinib, nilotinib and dasatinib, with dasatinib the most potent based on large scale phosphpopeptide screening assays. (Day et al., Eur J Pharmacol, 2008. 599(1-3): 44-53; Davies, H., et al., Cancer Res, 2005. 65(17): 7591-5)

In some embodiments, the methods include determining the sequence of all or part of the DDR2 gene in a sample comprising cells, e.g., tumor cells, from the subject, and comparing the sequence to a reference DDR2 gene or mRNA sequence. In some embodiments, the methods include sequencing all or part of the gene. The sequence of the DDR2 gene is known in the art and is provided at GenBank Accession No. NG_016290.1. In some embodiments, the methods include sequencing the coding region of the DDR2 gene; two transcript variants exist, variant (1) (GenBank Acc. No. NM_001014796.1) and variant (2) (GenBank Acc. No. NM_006182.2), which differs in the 5' UTR compared to variant 1. Both encode the same protein, i.e., GenBank Acc. No. NP_001014796.1 or NP_006173.2, which both set forth the following sequence:

```
                                                             (SEQ ID NO: 1)
  1 MILIPRMLLV LFLLLPILSS AKAQVNPAIC RYPLGMSGGQ IPDEDITASS QWSESTAAKY

61 GRLDSEEGDG AWCPEIPVEP DDLKEFLQID LHTLHFITLV GTQGRHAGGH GIEFAPMYKI
```

```
121 NYSRDGTRWI SWRNRHGKQV LDGNSNPYDI FLKDLEPPIV ARFVRFIPVT DHSMNVCMRV

181 ELYGCVWLDG LVSYNAPAGQ QFVLPGGSII YLNDSVYDGA VGYSMTEGLG QLTDGVSGLD

241 DFTQTHEYHV WPGYDYVGWR NESATNGYIE IMFEFDRIRN FTTMKVHCNN MFAKGVKIFK

301 EVQCYFRSEA SEWEPNAISF PLVLDDVNPS ARFVTVPLHH RMASAIKCQY HFADTWMMFS

361 EITFQSDAAM YNNSEALPTS PMAPTTYDPM LKVDDSNTRI LIGCLVAIIF ILLAIIVIIL

421 WRQFWQKMLE KASRRMLDDE MTVSLSLPSD SSMFNNNRSS SPSEQGSNST YDRIFPLRPD

481 YQEPSRLIRK LPEFAPGEEE SGCSGVVKPV QPSGPEGVPH YAEADIVNLQ GVTGGNTYSV

541 PAVTMDLLSG KDVAVEEFPR KLLTFKEKLG EGQFGEVHLC EVEGMEKFKD KDFALDVSAN

601 QPVLVAVKML RADANKNARN DFLKEIKIMS RLKDPNIIHL LAVCITDDPL CMITEYMENG

661 DLNQFLSRHE PPNSSSSDVR TVSYTNLKFM ATQIASGMKY LSSLNFVHRD LATRNCLVGK

721 NYTIKIADFG MSRNLYSGDY YRIQGRAVLP IRWMSWESIL LGKFTTASDV WAFGVTLWET

781 FTFCQEQPYS QLSDEQVIEN TGEFFRDQGR QTYLPQPAIC PDSVYKLMLS CWRRDTKNRP

841 SFQEIHLLLL QQGDE
```

In some embodiments, all or part of the DDR2 nucleic acid sequence is "translated" into a predicted amino acid sequence based on known rules of codon-amino acid specification. This predicted amino acid sequence can be evaluated for the presence of one or more differences from the reference amino acid sequence. In some embodiments, the presence of a missense mutation, e.g., a non-conservative variant, as compared to a wild-type reference (e.g., SEQ ID NO:1) in the amino acid sequence indicates an increased likelihood of response to a TKI. In some embodiments, a variant amino acid sequence is detected directly, e.g., using methods known in the art, such as methods using antibodies that bind specifically to a variant of DDR2 protein but not to wild-type, or by direct sequencing of the protein, e.g., using mass spectrometry analysis or other methods known in the art.

Figure 1B:
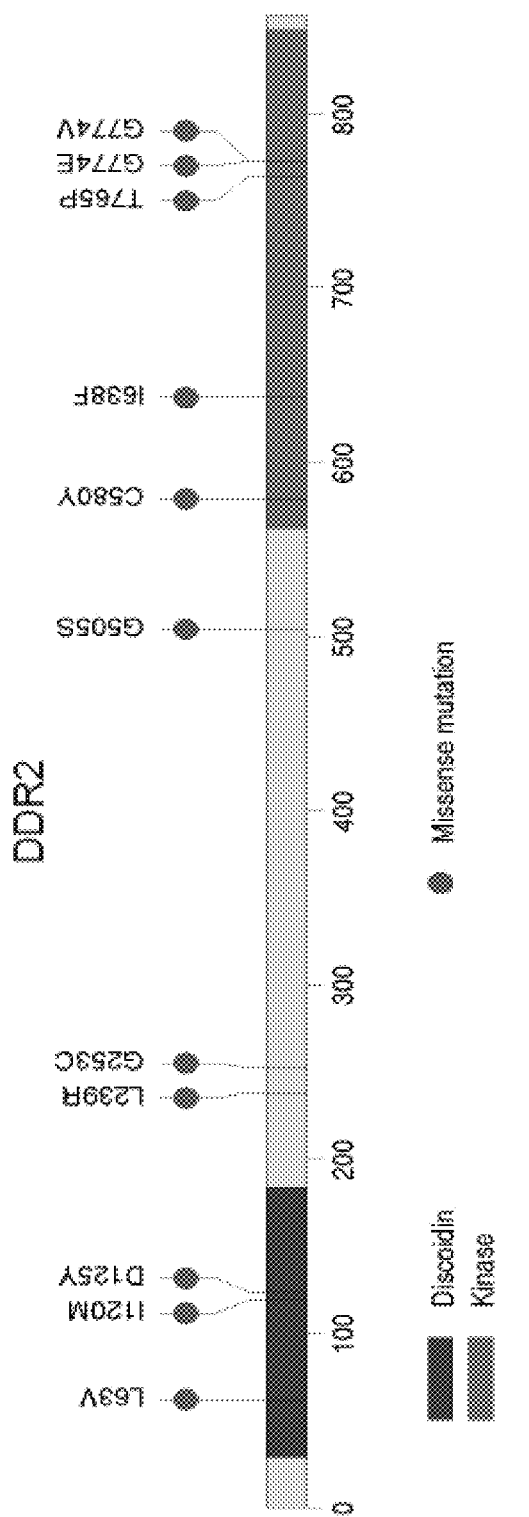
Figure 1C:
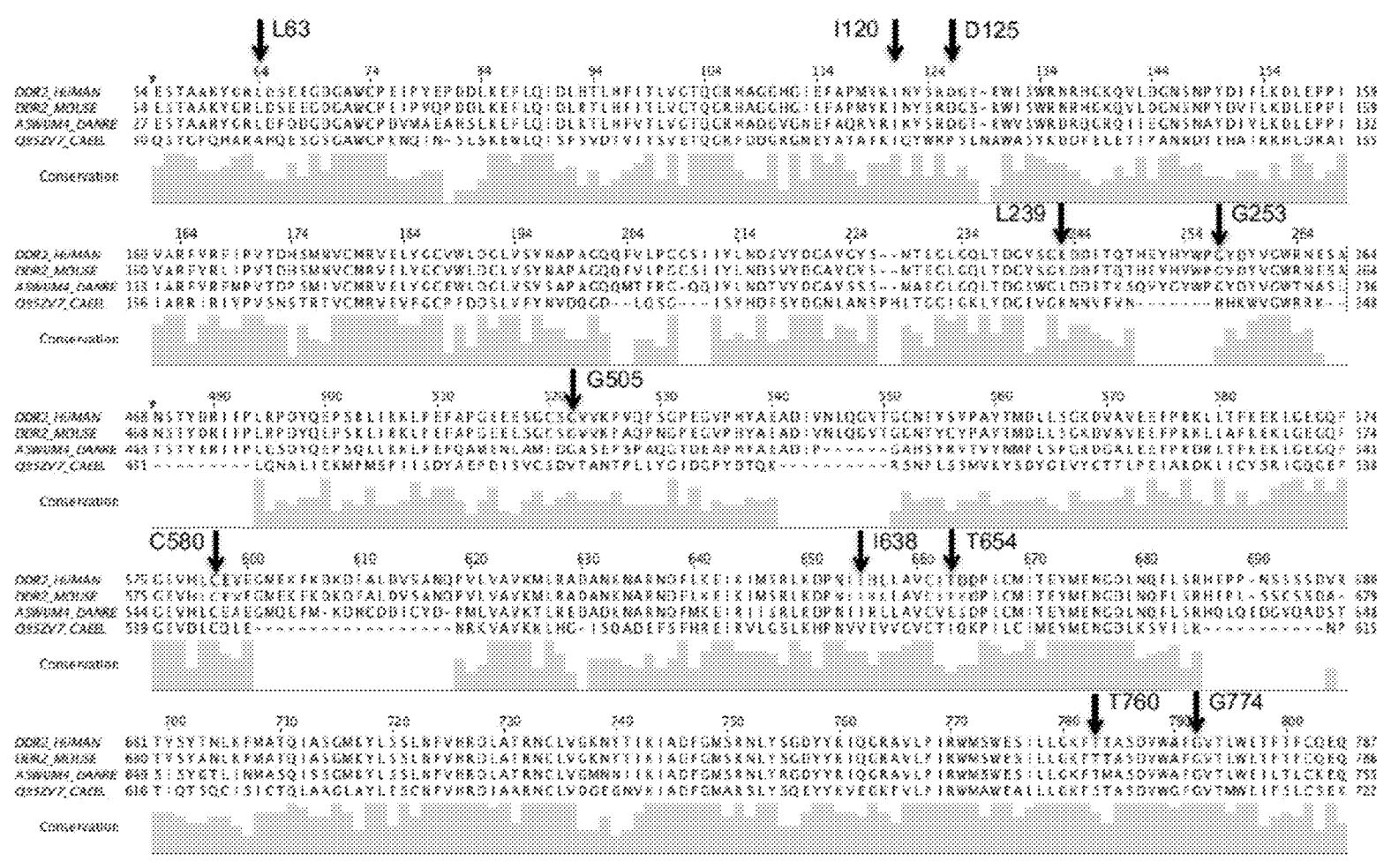

The methods can include the detection of specific mutations described herein, e.g., as shown in FIG. 1B or 1C, that alter the primary sequence of the DDR2 protein, e.g., L63V, I120M, D125Y, L239R, G253C, G5055, C580Y, I638F, T765P, G774E/V, and/or S768R.

Alternatively, the methods can include the detection of other mutations that alter the primary sequence of the DDR2 protein (e.g., missense or non-conservative mutations), or that do not alter the primary sequence of the DDR2 protein but affect levels of expression and/or half-life of the protein. In some embodiments, the methods include detecting mutations that alter the primary sequence of the DDR2 protein and affect kinase activity of the protein. Mutations that affect expression levels, half-life, or kinase activity can be identified readily by one of skill in the art, e.g., using assays known in the art and/or described herein. For example, in some embodiments a recombinant protein is produced using known molecular biological techniques, e.g., obtaining a wild type or reference sequence (e.g., genomic or cDNA), using mutagenesis (e.g., site-directed mutagenesis) to alter the sequence to reflect the mutation, and expressing the mutated protein in a cell, e.g., a mammalian cell, and assaying for protein levels and/or activity of the protein.

In some embodiments, the mutations are in the discoidin domain, e.g., amino acids 30-185 or 32-184 of NP_001014796.1; or the catalytic/kinase domain, e.g., amino acids 557-851 or 563-849 of NP_001014796.1.

As in preferred embodiments the methods described herein will be performed on human subjects, the human DDR2 gene sequence has been provided as an example. As one of skill in the art will appreciate, if the methods are performed on subjects of other species, a reference DDR2 sequence obtained from that species should be used.

In some embodiments, to identify a DDR2 reference sequence, a biological sample that includes non-cancerous nucleated cells (such as blood, a cheek swab, or mouthwash) is prepared and analyzed for sequence, or for the presence or absence of preselected markers. In some embodiments, direct analysis of DDR2 proteins is used to detect the presence of mutations, using samples comprising DDR2 proteins from the subject, e.g., tissue samples, e.g., from a tissue biopsy; in some embodiments, a SCC biopsy is used. Such determinations can be performed using methods known in the art by diagnostic laboratories, or, alternatively, diagnostic kits can be manufactured and sold to health care providers or to private individuals for self-diagnosis; such kits can include primers, probes, or antibodies that bind specifically to a mutation in DDR2. Diagnostic or prognostic tests can be performed as described herein or using well known techniques, such as described in U.S. Pat. No. 5,800,998. The presence or absence of a DDR2 variant in a subject may be ascertained by using any of the methods described herein. In some cases, results of these tests, and optionally interpretive information, can be returned to the subject or the health care provider. Information gleaned from the methods described herein can also be used to select or stratify subjects for a clinical trial. For example, the presence of a selected allelic variant described herein can be used to select or exclude a subject for participation in a clinical trial, e.g., a trial of a treatment for SCC, e.g., using a TKI.

The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples.

In some cases, the biological sample is processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., *Current Protocols in Molecular Biology*, eds., John Wiley & Sons (2003). The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAAMP® Tissue Kit (Qiagen, Chatsworth, Calif.) and the WIZARD® Genomic DNA purification kit (Promega).

The absence or presence of a variant DDR2 associated with TKI SENSITIVITY as described herein can be determined using methods known in the art. For example, gel electrophoresis, capillary electrophoresis, size exclusion chromatography, sequencing, and/or arrays can be used to detect the presence or absence of a variant DDR2. Amplification of nucleic acids, where desirable, can be accomplished using methods known in the art, e.g., PCR. In one example, a sample (e.g., a sample comprising genomic DNA), is obtained from a subject. The DNA in the sample is then examined to identify a variant DDR2 as described herein. The presence of the variant DDR2 can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular variant.

Other methods of nucleic acid analysis can include direct manual sequencing (Church and Gilbert, *Proc. Natl. Acad. Sci. USA* 81:1991-1995 (1988); Sanger et al., *Proc. Natl. Acad. Sci. USA* 74:5463-5467 (1977); Beavis et al., U.S. Pat. No. 5,288,644); automated fluorescent sequencing; single-stranded conformation polymorphism assays (SSCP) (Schafer et al., *Nat. Biotechnol.* 15:33-39 (1995)); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., *Proc. Natl. Acad. Sci. USA* 86:232-236 (1989)); denaturing high performance liquid chromatography (DHPLC, Underhill et al., *Genome Res.* 7:996-1005 (1997)); infrared matrix-assisted laser desorption/ionization (IR-MALDI) mass spectrometry (WO 99/57318); mobility shift analysis (Orita et al., *Proc. Natl. Acad. Sci. USA* 86:2766-2770 (1989)); restriction enzyme analysis (Flavell et al., *Cell* 15:25 (1978); Geever et al., *Proc. Natl. Acad. Sci. USA* 78:5081 (1981)); quantitative real-time PCR (Raca et al., *Genet Test* 8(4):387-94 (2004)); heteroduplex analysis; chemical mismatch cleavage (CMC) (Cotton et al., *Proc. Natl. Acad. Sci. USA* 85:4397-4401 (1985)); RNase protection assays (Myers et al., *Science* 230:1242 (1985)); use of polypeptides that recognize nucleotide mismatches, e.g., *E. coli* mutS protein; allele-specific PCR, and combinations of such methods. See, e.g., Gerber et al., U.S. Pat. Publication No. 2004/0014095 which is incorporated herein by reference in its entirety.

Sequence analysis can also be used to detect specific polymorphic variants. For example, polymorphic variants can be detected by sequencing exons, introns, 5' untranslated sequences, or 3' untranslated sequences. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined. Real-time pyrophosphate DNA sequencing is yet another approach to detection of polymorphisms and polymorphic variants (Alderborn et al., *Genome Research* 10(8):1249-1258 (2000)). Additional methods include, for example, PCR amplification in combination with denaturing high performance liquid chromatography (dHPLC) (Underhill et al., *Genome Research* 7(10):996-1005 (1997)).

In some embodiments, the methods described herein include determining the sequence of the entire region of the DDR2 locus described herein as being of interest. For example, a method provided herein can include determining a nucleic acid sequence of a DDR2 gene in a sample from a human subject, determining an expected amino acid translation of nucleic acid sequence; and comparing the expected amino acid translation with a reference amino acid sequence. In such a method, the presence of at least one amino acid variant (e.g., a non-conservative amino acid substitution) relative to the reference amino acid sequence can be indicative of TKI sensitivity or an increased likelihood of response to a TKI, or emergence of resistance to a TKI, in the human subject. For example, an amino acid variant can comprise a non-conservative substitution described herein. In some embodiments, the sequence is determined on both strands of DNA.

In order to detect sequence variants, it may be desirable to amplify a portion of genomic DNA (gDNA) or cDNA encompassing the variant site. Such regions can be amplified and isolated by PCR using oligonucleotide primers designed based on genomic and/or cDNA sequences that flank the site. PCR refers to procedures in which target nucleic acid (e.g., genomic DNA) is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. See e.g., *PCR Primer: A Laboratory Manual*, Dieffenbach and Dveksler, (Eds.); McPherson et al., *PCR Basics: From Background to Bench* (Springer Verlag, 2000); Mattila et al., *Nucleic Acids Res.*, 19:4967 (1991); Eckert et al., *PCR Methods and Applications*, 1:17 (1991); *PCR* (eds. McPherson et al., IRL Press, Oxford); and U.S. Pat. No. 4,683,202. Other amplification methods that may be employed include the ligase chain reaction (LCR) (Wu and Wallace, *Genomics* 4:560 (1989), Landegren et al., *Science* 241:1077 (1988), transcription amplification (Kwoh et al., *Proc. Natl. Acad. Sci. USA* 86:1173 (1989)), self-sustained sequence replication (Guatelli et al., *Proc. Nat. Acad. Sci. USA* 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth, Minn.), MacVector (Kodak/IBI), and the GCG suite of sequence analysis programs (Genetics Computer Group, Madison, Wis. 53711).

In some cases, PCR conditions and primers can be developed that amplify a product only when the variant allele is present or only when the wild type allele is present (MSPCR or allele-specific PCR). For example, subject DNA and a control can be amplified separately using either a wild type primer or a primer specific for the variant allele. Each set of reactions is then examined for the presence of amplification products using standard methods to visualize the DNA. For example, the reactions can be size-separated by agarose gel electrophoresis and the DNA visualized by staining with ethidium bromide or other DNA intercalating dye. In DNA samples from heterozygous subjects, reaction products would be detected in each reaction.

Real-time quantitative PCR can also be used to determine copy number. Quantitative PCR permits both detection and quantification of specific DNA sequence in a sample as an absolute number of copies or as a relative amount when normalized to DNA input or other normalizing genes. A key feature of quantitative PCR is that the amplified DNA product is quantified in real-time as it accumulates in the reaction after each amplification cycle. Methods of quantification can include the use of fluorescent dyes that intercalate with double-stranded DNA, and modified DNA oligonucleotide probes that fluoresce when hybridized with a complementary DNA.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant conferring TKI sensitivity or resistance.

In some cases, allele-specific oligonucleotides can also be used to detect the presence of a variant. For example, variants can be detected by performing allele-specific hybridization or allele-specific restriction digests. Allele specific hybridization is an example of a method that can be used to detect sequence variants, including complete haplotypes of a subject (e.g., a mammal such as a human). See Stoneking et al., *Am. J. Hum. Genet.* 48:370-382 (1991); and Prince et al., *Genome Res.* 11:152-162 (2001). An "allele-specific oligonucleotide" (also referred to herein as an "allele-specific oligonucleotide probe") is an oligonucleotide that is specific for a particular polymorphism can be prepared using standard methods (see Ausubel et al., *Current Protocols in Molecular Biology*, supra). Allele-specific oligonucleotide probes typically can be approximately 10-50 base pairs, preferably approximately 15-30 base pairs, that specifically hybridize to a nucleic acid region that contains a polymorphism. Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. In some cases, dot-blot hybridization of amplified oligonucleotides with allele-specific oligonucleotide (ASO) probes can be performed. See, for example, Saiki et al., *Nature* (London) 324:163-166 (1986).

In some embodiments, allele-specific restriction digest analysis can be used to detect the existence of a variant, if the variants result in the creation or elimination of a restriction site. Allele-specific restriction digests can be performed in the following manner. A sample containing genomic DNA is obtained from the individual and genomic DNA is isolated for analysis. For nucleotide sequence variants that introduce a restriction site, restriction digest with the particular restriction enzyme can differentiate the alleles. In some cases, polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a variant and is therefore indicative of the presence or absence of TKI sensitivity or resistance. For sequence variants that do not alter a common restriction site, mutagenic primers can be designed that introduce a restriction site when the variant allele is present or when the wild type allele is present. For example, a portion of a nucleic acid can be amplified using the mutagenic primer and a wild type primer, followed by digest with the appropriate restriction endonuclease.

In some embodiments, fluorescence polarization template-directed dye-terminator incorporation (FP-TDI) is used to determine which of multiple polymorphic variants of a polymorphism is present in a subject (Chen et al., *Genome Research* 9(5):492-498 (1999)). Rather than involving use of allele-specific probes or primers, this method employs primers that terminate adjacent to a variant site, so that extension of the primer by a single nucleotide results in incorporation of a nucleotide complementary to the polymorphic variant at the polymorphic site.

In some cases, DNA containing an amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe to DNA from the subject is indicative of TKI resistance or sensitivity.

The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a variant other than the reference sequence. If multiple variants exist at a site, this can be appropriately indicated by specifying which ones are present in the subject. Any of the detection means described herein can be used to determine the genotype of a subject with respect to one or both copies of the variant present in the subject's genome.

Methods of nucleic acid analysis to detect variants can include, e.g., microarray analysis. Hybridization methods, such as Southern analysis, Northern analysis, or in situ hybridizations, can also be used (see Ausubel et al., *Current Protocols in Molecular Biology*, eds., John Wiley & Sons (2003)). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

In some embodiments, it is desirable to employ methods that can detect the presence of multiple variants (e.g., variants at a plurality of sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel can also be performed so as to detect the presence of multiple variants (e.g., variants at a plurality of polymorphic sites) in parallel or substantially simultaneously.

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70% (e.g., 80%, 90%, 95%, 98% or more) identity to the target sequence. The probe sequence must also be sufficiently long so that the probe exhibits selectivity for the target sequence over non-target sequences. For example, the probe will be at least 20 (e.g., 25, 30, 35, 50, 100, 200, 300, 400, 500, 600, 700, 800, 900 or more) nucleotides in length. In some embodiments, the probes are not more than 30, 50, 100, 200, 300, 500, 750, or 1000 nucleotides in length. Probes are typically about 20 to about $1\times10^6$ nucleotides in length. Probes include primers, which generally refers to a single-stranded oligonucleotide probe that can act as a point of initiation of template-directed DNA synthesis using methods such as polymerase chain reaction (PCR), ligase chain reaction (LCR), etc., for amplification of a target sequence.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially such from Applied Biosystems, e.g., the Assays-on-Demand SNP kits. Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via PCR. See, for example, Nath and Johnson, *Biotechnic. Histochem.* 73(1):6-22 (1998); Wheeless et al., *Cytometry* 17:319-326 (1994); and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), TEXAS RED™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4, 4-difluoro-5,7-dimethyl-4-bora-3a,4a diaza-3-indacenepropionic acid, eosin-5-isothiocyanate, erythrosin-5-isothiocyanate, and CASCADE™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^3H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

In another aspect, the invention features arrays that include a substrate having a plurality of addressable areas, and methods of using them. At least one area of the plurality includes a nucleic acid probe that binds specifically to a sequence comprising a variant described herein, and can be used to detect the absence or presence of said variant, e.g., one or more SNPs, microsatellites, minisatellites, or indels, as described herein, e.g., to determine a haplotype comprising a plurality of variants. For example, the array can include one or more nucleic acid probes that can be used to detect a variant described herein. In some embodiments, the array further includes at least one area that includes a nucleic acid probe that can be used to specifically detect another marker associated with TKI resistance or sensitivity, as described herein. In some embodiments, the probes are nucleic acid capture probes.

Generally, microarray hybridization is performed by hybridizing a nucleic acid of interest (e.g., a nucleic acid encompassing a polymorphic site) with the array and detecting hybridization using nucleic acid probes. In some cases, the nucleic acid of interest is amplified prior to hybridization. Hybridization and detecting are generally carried out according to standard methods. See, e.g., Published PCT Application Nos. WO 92/10092 and WO 95/11995, and U.S. Pat. No. 5,424,186. For example, the array can be scanned to determine the position on the array to which the nucleic acid hybridizes. The hybridization data obtained from the scan is typically in the form of fluorescence intensities as a function of location on the array.

Arrays can be formed on substrates fabricated with materials such as paper, glass, plastic (e.g., polypropylene, nylon, or polystyrene), polyacrylamide, nitrocellulose, silicon, optical fiber, or any other suitable solid or semisolid support, and can be configured in a planar (e.g., glass plates, silicon chips) or three dimensional (e.g., pins, fibers, beads, particles, microtiter wells, capillaries) configuration. Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. Oligonucleotide probes forming an array may be attached to a substrate by any number of techniques, including, without limitation, (i) in situ synthesis (e.g., high-density oligonucleotide arrays) using photolithographic techniques; (ii) spotting/printing at medium to low density on glass, nylon or nitrocellulose; (iii) by masking, and (iv) by dot-blotting on a nylon or nitrocellulose hybridization membrane. Oligonucleotides also can be non-covalently immobilized on a substrate by hybridization to anchors, by means of magnetic beads, or in a fluid phase such as in microtiter wells or capillaries.

Arrays can include multiple detection blocks (i.e., multiple groups of probes designed for detection of particular variants). Such arrays can be used to analyze multiple different variants. Detection blocks may be grouped within a single array or in multiple, separate arrays so that varying conditions (e.g., conditions optimized for particular variants) may be used during the hybridization. For example, it may be desirable to provide for the detection of those variants that fall within G-C rich stretches of a genomic sequence, separately from those falling in A-T rich segments. General descriptions of using oligonucleotide arrays for detection of variants can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample (e.g., a portion of genomic DNA that includes at least a portion of human chromosome 14q32 (e.g., a region between SNPs rs3783397 and rs6576201) and/or optionally, a different portion of genomic DNA (e.g., a portion that includes a different portion of a human chromosome (e.g., including another region associated with TKI resistance or sensitivity)), and detecting binding of a nucleic acid from the sample to the array. Optionally, the method includes amplifying nucleic acid from the sample, e.g., genomic DNA that includes at least a portion of an IFN2 gene, and, optionally, a region that includes another region associated with TKI resistance or sensitivity, prior to or during contact with the array.

In some aspects, the methods described herein can include using an array that can ascertain differential expression patterns or copy numbers of one or more genes in samples from normal and affected individuals (see, e.g., Redon et al., *Nature* 444(7118):444-54 (2006)). For example, arrays of probes to a marker described herein can be used to measure variants between DNA from a subject having TKI sensitive SCC and control DNA, e.g., DNA obtained from an individual that does not have TKI sensitive SCC. Since the clones on the array contain sequence tags, their positions on the array are accurately known relative to the genomic sequence. Different hybridization patterns between DNA from an individual with TKI sensitive SCC and DNA from a normal individual at areas in the array corresponding to markers in the human chromosome 14q32 locus as described herein, and, optionally, one or more other regions associated with TKI sensitive SCC, are indicative of sensitivity to the TKI. Methods for array production, hybridization, and analysis are described, e.g., in Snijders et al., *Nat. Genet.* 29:263-264 (2001); Klein et al., *Proc. Natl. Acad. Sci. USA* 96:4494-99 (1999); Albertson et al., *Breast Cancer Res. and Treatment* 78:289-298 (2003); and Snijders et al. "BAC microarray based comparative genomic hybridization," in Zhao et al. (eds), *Bacterial Artificial Chromosomes: Methods and Protocols*, Methods in Molecular Biology, Humana Press, 2002.

Tyrosine Kinase Inhibitors (TKIs)

Upon identification of a subject as having a tumor with one or more DDR2 mutations as described herein, the methods can include administering a therapeutically effective amount of one or more tyrosine kinase inhibitors. TKIs useful in the methods described herein can include Axitinib (INLYTA; Pfizer), Critozinib (XALKORI; Pfizer), Dasatinib (SPRYCEL; BMS), Erlotinib (TARCEVA; Roche, Astellas), Gefitinib (IRESSA; Astra Zeneca), Imatinib (GLEEVEC; Novartis), Lapatinib (TYKERB; GSK), Nilotinib (TASIGNA; Novartis), Pazopanib (VOTRIENT; GSK), Ruxolitinib (JAKAFI; Incyte, Novartis), Sorafenib (NEXAVAR; Bayer/Onyx), Sunitinib (SUTENT; Pfizer), Vandetanib (CAPRELSA/ZACTIMA; Astra Zeneca), ponatinib (AP24534; ARIAD); Vemurafanib (ZELBORAF; Roche/Daiichi Sankyo), lapatinib (GW-572016), canertinib (CI-1033), semaxinib (SU5416), vatalanib (PTK787/ZK222584), sorafenib (BAY 43-9006), sutent (SU11248), and leflunomide (SU101). In preferred embodiments, the TKI is dasatinib, nilotinib, imatinib, and/or ponatinib.

SPRYCEL (dasatinib, Bristol-Myers Squibb [BMS]-354825) is a potent, broad spectrum inhibitor of 5 critical oncogenic tyrosine kinases/kinase family members (BCR-ABL, SRC, c-KIT, PDGF receptor β [PDGFRβ], and ephrin [EPH] receptor kinases), each of which are activated in multiple forms of human malignancies, and was discovered and developed by BMS. The chemical name for dasatinib is N-(2-chloro-6-methylphenyl)-2-[[6-[4-(2-hydroxyethyl)-1-piperazinyl]-2-methyl-4-pyrimidinyl]amino]-5-thiazolecarboxamide, monohydrate. The molecular formula is $C_{22}H_{26}ClN_7O_2S.H2O$, which corresponds to a formula weight of 506.02 (monohydrate). The anhydrous free base has a molecular weight of 488.01. SPRYCEL is approved in the United States (US)i, Europe (EU), and several other countries for the treatment of adults in all phases of chronic myeloid leukemia (CML) with resistance or intolerance to prior therapy including imatinib, and in patients with Philadelphia chromosome positive acute lymphoblastic leukemia (Ph+ ALL) who are resistant or intolerant to prior therapy.

Pharmaceutical compositions including TKIs, as well as dosage and routes of administration, are known in the art or can be determined using routine experimentation.

For example, the recommended starting dosage of dasatinib for adults with chronic phase CML is 100 mg administered orally once daily (QD). The recommended starting dosage for accelerated phase CML, myeloid or lymphoid blast phase CML, or Ph+ ALL is 140 mg/day administered orally once daily. In clinical studies of adult CML and Ph+ ALL patients, dose escalation to 140 mg once daily (chronic phase CML) or 180 mg once daily (advanced phase CML and Ph+ ALL) was allowed in patients who did not achieve a hematologic or cytogenetic response at the recommended starting dosage.

EXAMPLES

The invention is further described in the following examples, which do not limit the scope of the invention described in the claims.

Materials and Methods

The following materials and methods were used in the Examples described herein.

Collection of Squamous Cell Lung Cancer Samples:

For the primary and secondary screens tumor samples were obtained under a general tissue collection protocol for patients with lung cancer who are consented to tissue collection for research, including DNA sequencing, prior to surgery. All patients with resectable biopsy-proven squamous cell lung cancers (as diagnosed by a board-certified Anatomic Pathologist) were eligible and eligible subjects underwent a detailed informed consent procedure prior to enrollment on the protocol which included a discussion of the use of tissue samples for DNA sequencing studies and written documentation of consent. In addition, DNA samples from de-identified squamous cell lung cancer patients were obtained from the Ontario Cancer Institute for the primary and secondary screens as part of a Dana Farber/Harvard Cancer Center IRB-approved collection of de-identified tumor samples for DNA sequencing studies. IRB approval for collection of de-identified samples was subject to a review of the local IRB-approved protocols for all external sites to ensure an adequate informed consent process had taken place.

The validation screen was performed as follows. Samples were collected in accordance with a tissue collection protocol approved by the University of Cologne Ethics Committee which involved a detailed informed consent process including a discussion of genetic testing prior to the subject's surgery with written documentation of consent. Again, all patients with biopsy-proven squamous cell lung cancer were eligible regardless of disease stage as long as their tumors were considered resectable. De-identified samples were also collected from additional European sites including Haukeland University Hospital, University Hospital Zurich, Université Joseph Fourier, Oslo University Hospital, Jena University Hospital and University Medical Centre Groningen. At all sites samples were obtained in accordance with an IRB approved tissue collection protocol and the collection of de-identified samples from these sites was approved by the University of Cologne Ethics Committee after a review of local collection protocols.

For the single patient sample obtained from the recent clinical trial of combination therapy with dasatinib and erlotinib for advanced lung cancer DNA was obtained under an IRB-approved protocol and the sequencing of the de-identified sample by both 454 and Sanger sequencing was performed with approval after a review of the collection protocol.

In all instances specimens were continuously selected at the site of surgery in order to avoid sampling bias and all samples were de-identified prior to processing for DDR2 sequencing. When available, de-identified correlative clinical data was provided with the samples, though this data was not available to the investigators prior to sample genotyping. Patients with a prior history of tumors involving a visceral organ site were excluded to avoid the inclusion of metastases.

DDR2 Sequencing.

DDR2 was sequenced from genomic DNA obtained from squamous lung cancer cell lines and patient samples by conventional Sanger sequencing. In the discovery set 20 patient samples and matched normal DNA were used for sequencing 201 genes including 90 kinases. All mutations were verified as somatic. Mutations were identified using an automated mutation caller and then verified manually with comparison made to the matched normal sequence in the case of all primary tumor samples. In the secondary screen 35 additional patient samples and 13 SCC cell lines were used for sequencing the six mutated tyrosine kinases identified in the primary screen (DDR2, FGFR2, NTRK2, JAK2, CDK8 and FLT3). In the validation screen 222 total samples underwent sequencing of the DDR2 gene. In all cases except D125Y matched normal DNA was available to verify the mutation as somatic.

Cell Culture.

A549, NCI-H2286, HCC-366 and NCI-H1703 cells were obtained from the core collection at the Dana Farber Cancer Institute, having previously been purchased from the ATCC and used to establish a collection of early passage lung cancer cell lines which were analyzed by fingerprinting and SNP arrays (32). All cells used for the experiments described in this manuscript were obtained from freezes made at that time. Lung cancer cell lines were grown in RPMI (Invitrogen) with 10% fetal calf serum, NIH-3T3 cells were grown in DMEM (Mediatech) with 10% serum and Ba/F3 cells in RPMI supplemented with 10% serum and IL-3 (BD Biosciences) at 10 ng/ml. For IL-3 withdrawal experiments Ba/F3 cells were collected via centrifugation, washed once in sterile PBS and then resuspended in media without IL-3. Colony formation assays in NIH-3T3 cells were performed in six-well plates in which 25,000 NIH-3T3 cells were plated in triplicate in 1 ml of 0.33% top agar on top of 2 ml of 0.5% bottom agar. After three weeks colonies were counted using the NIH ImageJ software.

Vectors.

The full-length DDR2 cDNA was obtained from Origene and cloned into the EcoRI site of the retroviral vector p-Wzl-Blast and p-Babe-puro following the addition of a c-terminal FLAG tag by PCR. Mutants were generated by site-directed mutagenesis using the Quickchange site directed mutagenesis kit (Strategene). All mutations were verified by sequencing. sh-RNA lentiviral vectors for DDR2 were obtained from The RNAi Consortium at the Broad Institute (46, 47). DDR2 sh-RNA-2 corresponds to TRC clone TRCN0000121117 with hairpin sequence 5'-CCGG-CCCATGCCTATGCCACTCCAT-CTCGAG-ATG-GAGTGGCATAGGCATGGG-TTTTTG-3' (SEQ ID NO:2) targeting the 3' UTR of DDR2. DDR2 sh-RNA-5 corresponds to TRC clone TRCN0000121121 with hairpin sequence 5'-CCGG-CCCTGGAGGTTCCATCATTTA-CTCGAG-TAAATGATGGAACCTCCAGGG-TTTTTG-3' (SEQ ID NO:3) targeting the coding sequence of DDR2. Both hairpins were provided in the pLKO vector. A hairpin targeting GFP (shGFP) was obtained from TRC as well and used as a control.

Viral Infections.

The DDR2 transgene was expressed in the lung cancer cell lines, NIH-3T3 cells and Ba/F3 cells using retroviral transduction with the pWzl vector, as has been previously described. Briefly, 293T cells were used to generate the virus with the appropriate pWzl or pBabe vector and packaging vector transfected using Fugene (Roche). Cells were subjected to two rounds of overnight infection in the presence of polybrene and stable cells generated using blasticidin selection at 10 mg/ml for 3T3, Ba/F3 and A549, 2 mg/ml NCI-H2286 and for NCI-H1703 and 1 mg/ml for HCC-366. Lentiviral infections were performed per the on-line TRC protocol (48) with 293T cells transfected with the suggested three vector combination of pLKO, VSVG and delta 8.9. Virus was collected and used to infect the lung cancer cell lines for six hours in the presence of polybrene. Stable cell lines were generated using puromycin selection at a concentration of 2 mg/ml for NCI-H2286 and 4 mg/ml for NCI-H1703, A549 and HCC-366.

Cell Proliferation and Viability Assays.

Cell proliferation was measured with the Cell-Titer-Glo reagent (Promega) per the manufacturer's instructions. For experiments with the SCC cell lines cells were plated in clear-bottomed 96 well plates at a density of 1500 cells per well. The following day the drug was added and cell proliferation was measured six days later for the SCC cell lines. For Ba/F3 cells were plated at 5000 cells per well and the drug added the same day. Proliferation was measured four days later. Proliferation measurements were made using a standard 96 well plate luminometer/plate reader. Data are shown as relative values in which the luminescence at a given drug concentration is compared to untreated cells of the same cell type. Kinase inhibitors were purchased from LC Labs or were synthesized by Nathanael Gray's laboratory at Harvard Medical School. In vitro IC50s for DDR2 were determined for all compounds by LanthaScreen TR-FRET kinase activity assays performed by Invitrogen. Cell viability was measured using a vi-Cell reader to stain cells with trypan blue and to generate 50 independent images for each measured sample Annexin V (BD Biosciences) analysis was performed on dasatinib treated cells 48 hours after addition of drug per the manufacturer's protocol. For sh-RNA experiments cells were plated at a density of 1500 cells per well in 96 well plates following puromycin selection. Proliferation was measured four days later as compared to cells expressing a hairpin targeting GFP.

Immunoblots:

Immunoblots were performed using the Nupage system (Invitrogen) per the manufacturer's protocol. Cells were lysed in 1% NP-40 with protease (Roche) and phosphatase inhibitors (Calbiochem) and protein concentration assayed with the Bradford reagent (Bio-Rad). Primary antibodies used were Flag-M2 (Sigma), phospho-Y417-Src (Cell Signaling Technologies), phospho-Y694-STAT5 (Cell Signaling) and Actin (Santa Cruz). A DDR2 antibody was generated for this project by Bethyl Labs. Secondary HRP-conjugated antibodies were all obtained from Pierce and proteins detected by pico-ECL (Thermo Scientific). Images were imported into Adobe Illustrator using an Epson 4490 scanner. In some cases brightness and/or contrast of the scanned images was adjusted for clarity and blots were cropped to display the area of interest in the displayed figures. In all cases adjustment of brightness or contrast the adjustment was applied uniformly to the image as a whole.

Xenografts:

All animal experiments were performed according to institutional guidelines regarding animal safety. Nude mice were injected with the lung cancer cell lines at a density of 2.5 (A549), 3.0 (NCI-H1703) or 5.0 (NCI-H2286 and HCC-366) million cells per injection to try to control for the variable rates of tumor growth in the animals. Cohorts of ten mice were injected at three sites for each cell type and the mice were observed until the tumor volume approached 150 cubic milliliters for A549 and NCI-H1703 or 100 cubic milliliters for NCI-H1703. At that time mice were treated with dasatinib at 50 mg/kg or vehicle control daily for two weeks and tumor size measured during the treatment period.

Statistics:

For proliferation and colony formation assays mean values from a minimum of triplicate samples are reported as well as standard errors as calculated by Microsoft Excel. $IC_{50}$ values were obtained using Graph Pad Prism software. Power and sample size calculations were performed using the Interactive Statistics Web Resource (43).

Example 1

DDR2 is Mutated in Squamous Cell Lung Cancer

Sanger sequencing of 201 genes, including the entire tyrosine kinome, was performed in an initial set of 20 primary lung SCC samples and matched normal controls. Somatic missense mutations were identified in 25 genes in this discovery sample set including six in tyrosine kinase genes (FIG. 1a). Recurrent somatic mutations were identified in TP53 (n=8), and in the tyrosine kinase genes: Discoidin Domain Receptor 2 (DDR2; n=2) and Kinase insert Domain Receptor (KDR; n=2) (FIG. 1a). Subsequent sequencing of six of the mutated tyrosine kinase genes (DDR2, FGFR2, NTRK2, JAK2, FLT3 and CDK8), selected on the basis of being possible therapeutic targets, in a secondary screen of 48 squamous cell lung cancer samples including 13 cell lines revealed four additional DDR2 mutations (FIG. 1a) as well as three FLT3 mutations, two NTRK2 and JAK2 mutations and one mutation in each of FGFR2 and CDK8.

Given that DDR2 was the most frequently mutated gene in the primary and secondary screen, DDR2 was sequenced in a validation cohort of 222 primary lung SCC samples which yielded an additional five samples with mutation, resulting in an overall frequency of 3.8% (n=11) in 290 total samples and an overall frequency of 3.2% in primary lung SCC samples when cell lines were excluded (n=9/277) (FIG. 1a). Mutations were found both in the kinase domain and in other regions of the protein sequence and two mutations were identified at G774 (FIG. 1b). The L239R and I638F mutations were identified in the HCC-366 and NCI-H2286 SCC cell lines, respectively, and the remainder of the mutations was found in primary SCC samples. The majority of the mutations resided in regions of high degrees of amino acid conservation as compared to the murine, zebrafish and *C. elegans* homologs of DDR2 (FIG. 1c). Additional genomic analysis of previously reported copy number and gene expression datasets did not reveal any evidence of DDR2 overexpression in SCCs as compared to normal lung or lung adenocarcinoma nor were any copy number alterations in DDR2 found (19, 22-24). A query of the limited clinical information accompanying the sequenced samples did not Identify any significant correlation of DDR2 mutation status with the age, sex or smoking status of the patients.

Example 2

DDR2 Mutant Cell Lines are Selectively Sensitive to Tyrosine Kinase Inhibitors and to Sh-RNA-Mediated Depletion of DDR2

To assess whether targeting DDR2 might be a promising therapeutic strategy in lung SCC, several tyrosine kinase inhibitors reported to inhibit DDR2 including imatinib and dasatinib, drugs which are FDA-approved for clinical use for targeting BCR-Abl in chronic myelogenous leukemia and acute lymphoblastic leukemia, c-KIT in gastrointestinal stromal tumors and PDGFR in chronic myelomonocytic leukemia (21, 25-28) were analyzed. Fluorescence resonance energy transfer (FRET) measurements provided in vitro $K_d$ values of dasatinib (5.4 nM) and imatinib (71.6 nM) for recombinant DDR2 (Table 1).

TABLE 1

Chemical structures and Kd for DDR2 for the compounds described in the manuscript.

| Compound | Structure | Kd (nM) |
| --- | --- | --- |
| Dasatinib | 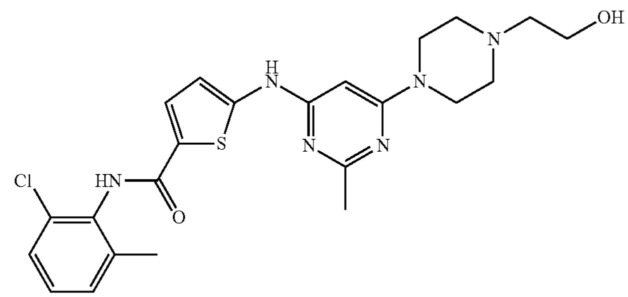 [SMILES: Cc1nc(Nc2ccc(C(=O)Nc3c(C)cccc3Cl)s2)cc(N2CCN(CCO)CC2)n1] | 5.4 |
| Imatinib | 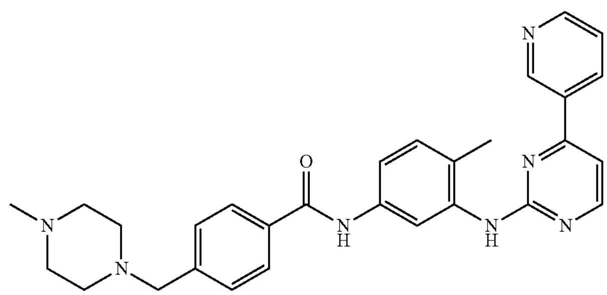 [SMILES: Cc1ccc(NC(=O)c2ccc(CN3CCN(C)CC3)cc2)cc1Nc1nccc(-c2cccnc2)n1] | 71.6 |
| Nilotinib | 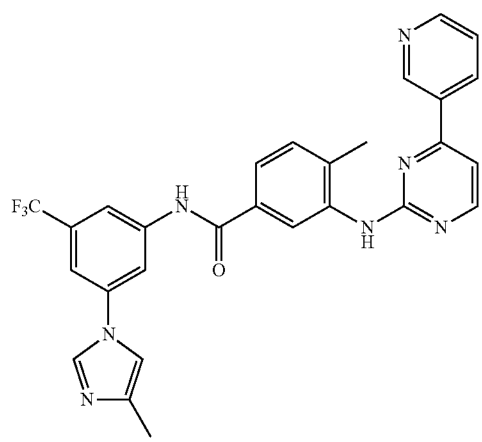 [SMILES: Cc1cn(-c2cc(NC(=O)c3ccc(C)c(Nc4nccc(-c5cccnc5)n4)c3)cc(C(F)(F)F)c2)cn1] | 35.4 |
| AZD0530 | 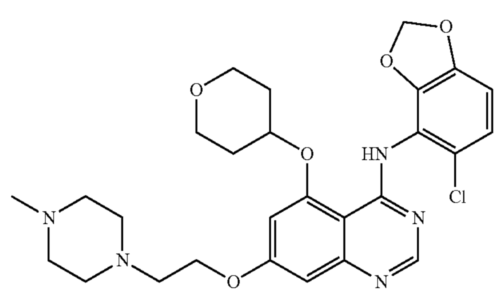 [SMILES: CN1CCN(CCOc2cc(OC3CCOCC3)c3c(Nc4c(Cl)ccc5c4OCO5)ncnc3c2)CC1] | 291 |

TABLE 1-continued

Chemical structures and Kd for DDR2 for the compounds described in the manuscript.

| Compound | Structure | Kd (nM) |
|---|---|---|
| AP24534 | 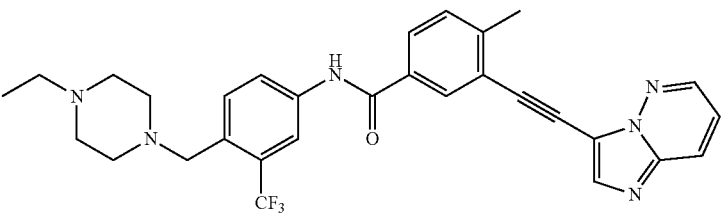 [SMILES: CCN1CCN(Cc2ccc(NC(=O)c3ccc(C)c(C#Cc4cnc5cccnn45)c3)cc2C(F)(F)F)CC1] | 8.99 |

Figure 2A:
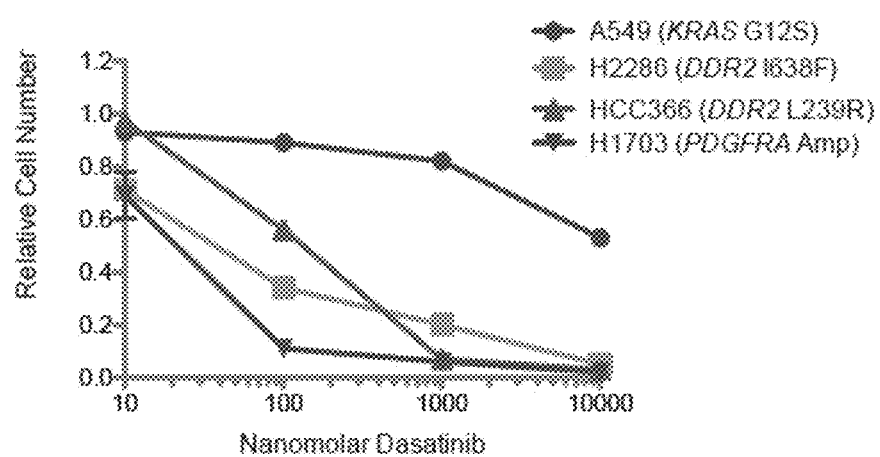
FIGS. 2a-d: Lung cancer cell lines with DDR2 mutations are sensitive to drugs and RNAi targeting DDR2. (a) Proliferation of A549, NCI-H2286, HCC-366 and NCI-H1703 grown for six days in the presence of various concentrations of dasatinib. Proliferation shown relative to untreated cells at the same time point. Standard errors are shown for triplicate samples. (b) Proliferation shown of NCI-H2286 and HCC-366 cell lines ectopically expressing the T654M gatekeeper mutation in DDR2, labeled as DDR2*. Six day proliferation in the presence of dasatinib is shown as above. For NCI-H2286 and HCC-366 the gatekeeper mutation is expressed in cis with the DDR2 mutation found in the cell line. (c) Proliferation measured as above for NCI-H2286, HCC-366 and NCI-H1703 cells stably expressing sh-RNA vectors targeting either GFP or the 3' UTR of DDR2 (DDR2 sh-RNA-2) or the coding sequence of DDR2 (DDR2 sh-RNA-5). Proliferation is measured after four days in culture as compared to day 1. Standard errors are shown for triplicate samples. Immunoblot showing relative levels of DDR2 in the cell lines used in the experiment is shown in the inset. "G" indicates cells expressing shGFP, and "2" and "5" the numbered DDR2 targeted hairpins. (d) Four-day proliferation of the DDR2 mutant NCI-H2286 and HCC-366 cell lines stably expressing ectopic DDR2 following knockdown of DDR2 by a sh-RNA targeting the 3' UTR of DDR2 (sh-RNA-2). Proliferation of triplicate samples is presented as above relative to cells transduced with a sh-RNA targeting GFP. Protein levels of DDR2 are shown in the immunoblot below, "G" indicates sh-GFP, "2" indicates expression of sh-RNA 2 and "D" indicates expression of sh-RNA2 and DDR2.
Figure 2B:
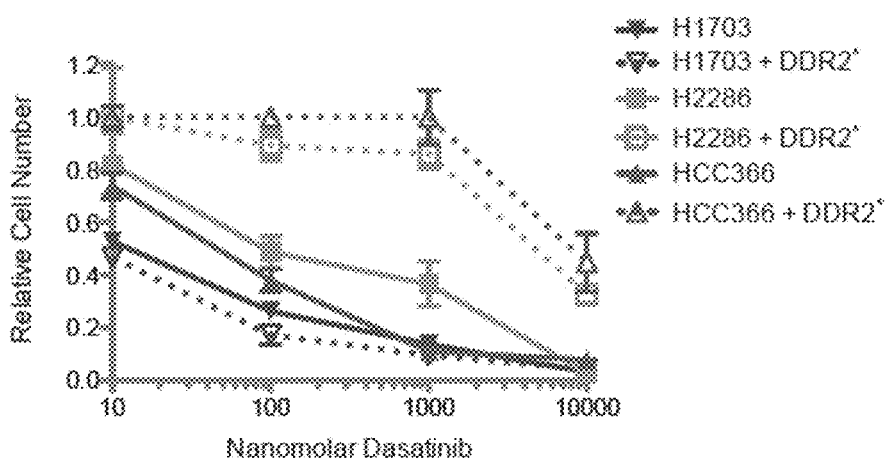
Figure 2C:
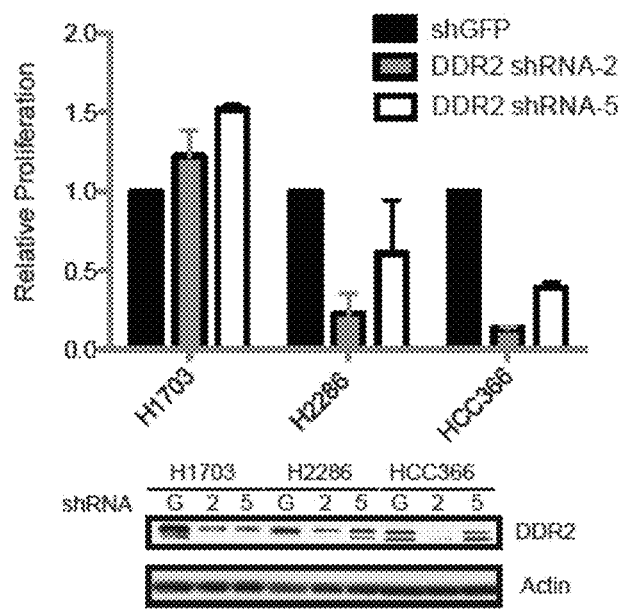
Figure 2D:
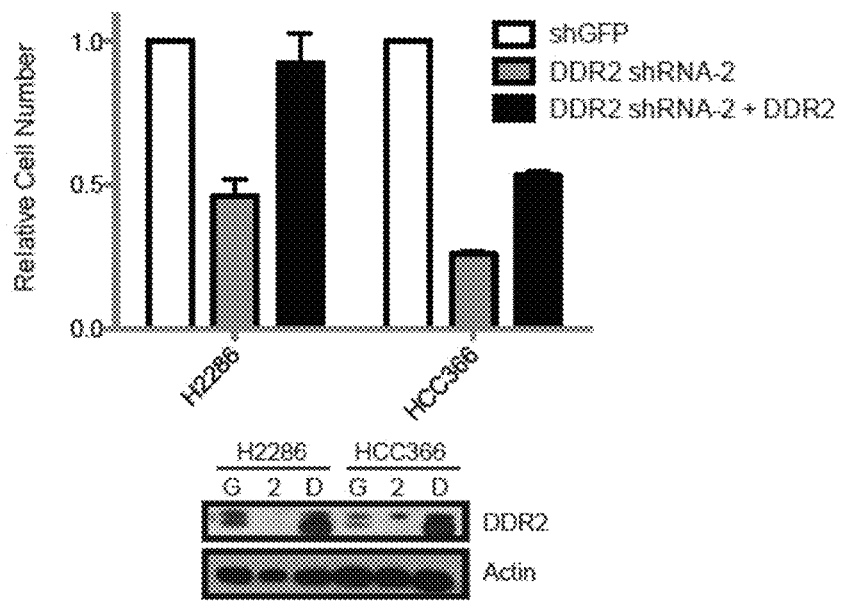
Figure 2E:
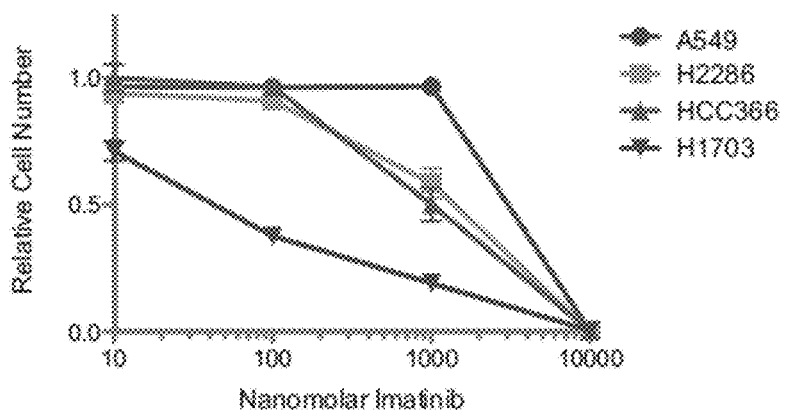
FIGS. 2e-i: Squamous lung cancer cell lines harboring DDR2 mutations are sensitive to tyrosine kinase inhibitor treatment. (e) Proliferation of A549, NCIH2286, HCC-366 and NCI-H1703 grown for six days in the presence of various concentrations of imatinib. Proliferation is presented relative to untreated cells at the same time point. Standard errors are presented for triplicate samples. (f) Viability measured by trypan blue exclusion in A549, NCI-H2286, HCC-366 and NCI-H1703 cells grown in the indicated concentrations of dasatinib. Data are presented as viability relative to untreated cells at the same time point and represent an average of fifty independently acquired trypan blue images in each of three replicates with standard errors shown. (g) Proliferation of A549, NCIH2286, HCC-366 and NCI-H1703 cells grown for six days in the presence of nilotinib. Data are presented as above. (h) Proliferation of A549, NCI-H2286, HCC-366 and NCI-H1703 cells grown in the presence of AP24534. Data are presented as above. (i) Immunoblot showing DDR2 expression from cell lines used in the experiment shown in FIG. 2c. DDR2* denotes the "gatekeeper" transgene.
Figure 2F:
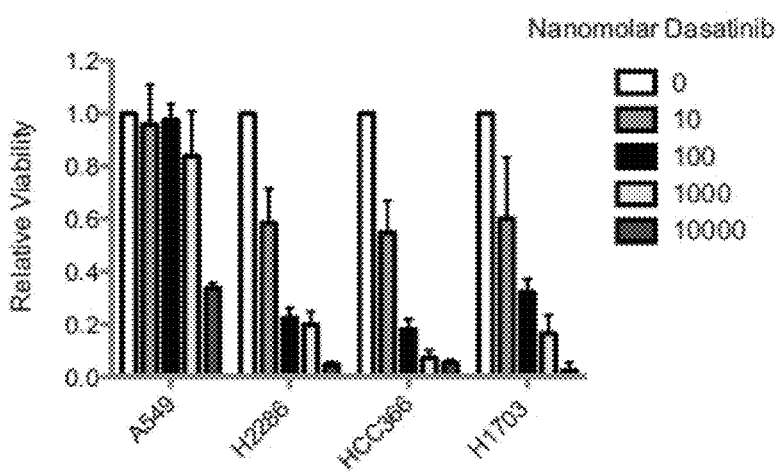

Dasatinib showed particular efficacy against SCC cell lines bearing DDR2 mutations, as dasatinib inhibited proliferation of the DDR2-mutant NCI-H2286 and HCC-366 cells with calculated $IC_{50s}$ of 139 and 140 nM respectively (FIG. 2a). Of note, a recent pharmacokinetic analysis of dasatinib in lung cancer patients demonstrated that peak concentrations of dasatinib were in the range of 300 ng/ml (615 nM) at the maximum tolerated dose of 140 mg daily, a dose approved for use in leukemias (29). Imatinib was less potent when tested in the same cell lines with respective $IC_{50s}$ of 1.2 and 1.0 mM for the DDR2-mutant NCI-H2286 and HCC-366 cell lines (FIG. 2e). Dasatinib and imatinib were less effective against the A549 cell line which is known to harbor a KRAS mutation and does not have any DDR2 mutations (calculated $IC_{50}$ of 7.4 mM for dasatinib and 2.3 mM for imatinib). Consistent with previous reports, the NCI-H1703 SCC cell line, which contains a PDGFRA amplification, was sensitive to both drugs, serving as a positive control for our assay (30, 31). Notably, no other somatic mutations have been reported in the COSMIC database for NCI-H2286 or HCC-366 lines to suggest alternative dasatinib targets and a previous report examining the drug sensitivities of 83 NSCLC cell lines identified HCC-366 as the most sensitive squamous cell lung cancer line to dasatinib, though NCI-H2286 and NCI-H1703 were not assayed (32). Treatment of the DDR2 mutant cell lines with dasatinib appeared to lead to cell death as opposed to cell cycle arrest as measured by trypan blue exclusion (FIG. 2O. Dasatinib treatment was associated with an increase in cellular annexin V staining, suggesting that the treated cells died by apoptosis.

Figure 2G:
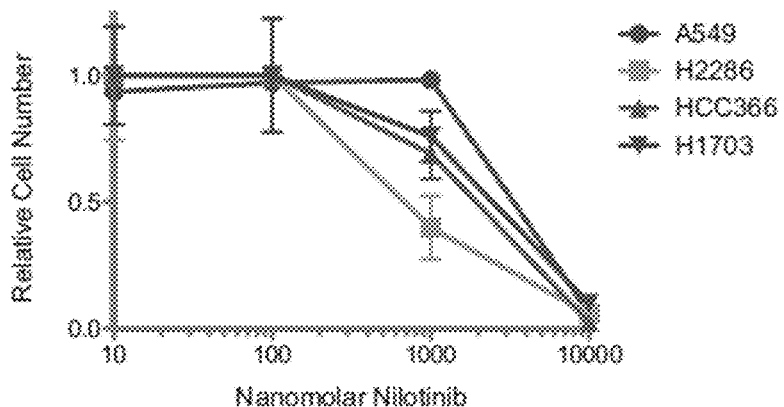
Figure 2H:
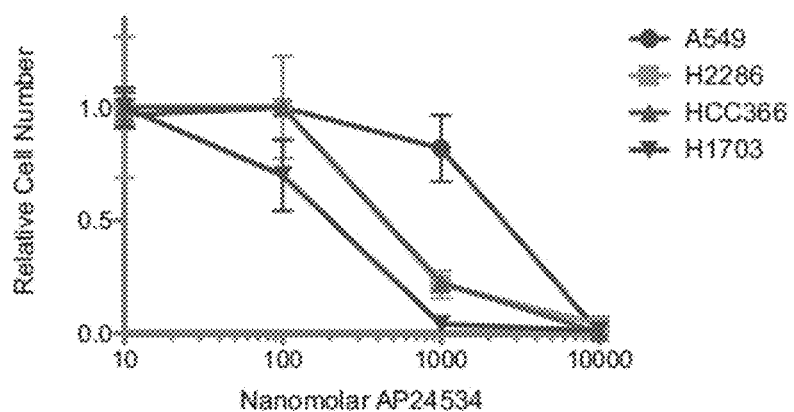
Figure 2I:
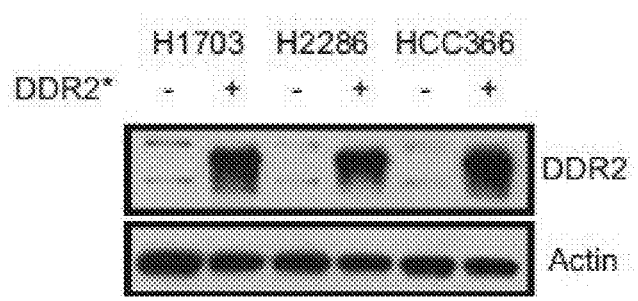

To validate DDR2 as a relevant target of dasatinib in SCCs a DDR2 transgene with a threonine to methionine mutation at amino acid 654, a mutation site shown previously to render DDR2 dasatinib-insensitive in a manner similar to the ability of the T790M mutation in EGFR to confer acquired resistance to the tyrosine kinase inhibitors erlotinib and gefitinib (33), was ectopically expressed. The dasatinib-insensitive DDR2 "gatekeeper" mutant was introduced in cis with the observed L239R and I638F mutations in the HCC-366 and NCI-H2286 cell lines respectively as well as alone in NCI-H1703. Expression of the gatekeeper mutation led to a decrease in dasatinib sensitivity in both DDR2 mutant cell lines and had a modest effect on NCI-H1703 (FIG. 2b; transgene expression is shown in FIG. 2i). While the calculated $IC_{50}$ for NCI-H1703 did not change with ectopic expression of the gatekeeper, the $IC_{50}$ increased by 35-fold for NCI-H2286 and 209-fold for HCC-366, respectively. Interestingly, a parallel sequencing project in our lab identified a T654I mutation in DDR2 in a primary endometrial carcinoma sample.

Dasatinib was originally designed as an inhibitor of Src and is a multi-targeted tyrosine kinase inhibitor (34). Dasatinib treatment is associated with toxicity in patients including myelosuppression and the development of pleural and pericardial effusions (35, 36). In an attempt to identify additional agents which could potently inhibit DDR2 with less associated toxicity we screened a panel of 20 tyrosine kinase inhibitors which were predicted to have the potential to inhibit DDR2 based on their respective structures. We found that nilotinib, a second-generation BCR-Abl inhibitor, as well as with AP24534, a third generation BCR-Abl inhibitor which displays activity against BCR-Abl and imatinib-resistant BCR-Abl (36), inhibited the proliferation of SCC lines harboring DDR2 mutations (FIGS. 2g and 2h). We observed that AP24534 treatment resulted in a greater degree of inhibition than nilotinib which was agreement with calculated in vitro $K_d$ values of 35.4 nM for nilotinib and 9.0 nM for AP24534 as compared to 5.4 nM for dasatinib (Table 1).

Example 3

Sh-RNAs Targeting DDR2 Kill DDR2-Mutant SCC Cell Lines

As an independent measure of DDR2-dependency short-hairpin RNAs targeting DDR2 were expressed using lentiviral vectors in the NCI-H2286, HCC-366 and NCI-H1703 cell lines. A set of sh-RNA-expressing plasmids was screened for the ability to knock-down DDR2 mRNA expression by real-time PCR in NCI-H2286 cells and selected two hairpins for further analysis given their ability to reduce DDR2 mRNA levels by approximately 50%. Knock-down of DDR2 by these two sh-RNAs led to a reduction in proliferation of the two DDR2 mutant cell lines but not of PDGFRA-amplified NCI-H1703 cells which had been sensitive to imatinib and dasatinib in our proliferation assays (FIG. 2c). The reduction in proliferation appeared to correlate with the degree of knock-down as the observed phenotype was greater with sh-RNA-2 than sh-RNA-5 (FIG. 2c) and appeared to be caused by cell death and not cell cycle arrest.

To assess the specificity of the observed knock-down phenotype a similar experiment was performed in NCI-H2286 and HCC-366 cells ectopically expressing their described mutated forms of DDR2 (I638F and L239R respectively); endogenous DDR2 was knocked-down with sh-RNA-2 which targets the 3' UTR of DDR2 and so would not be expected to interfere with ectopic expression of DDR2. For both NCI-H2286 and HCC-366, ectopic expression of DDR2 attenuated the anti-proliferative effect of endogenous DDR2 knock-down and the effect was of greater magnitude in NCI-H2286, perhaps due to a greater degree of off-target effects in HCC-366 (FIG. 2d).

Example 4

DDR2 Mutations are Associated with Dasatinib Sensitivity In Vivo

Figure 3:
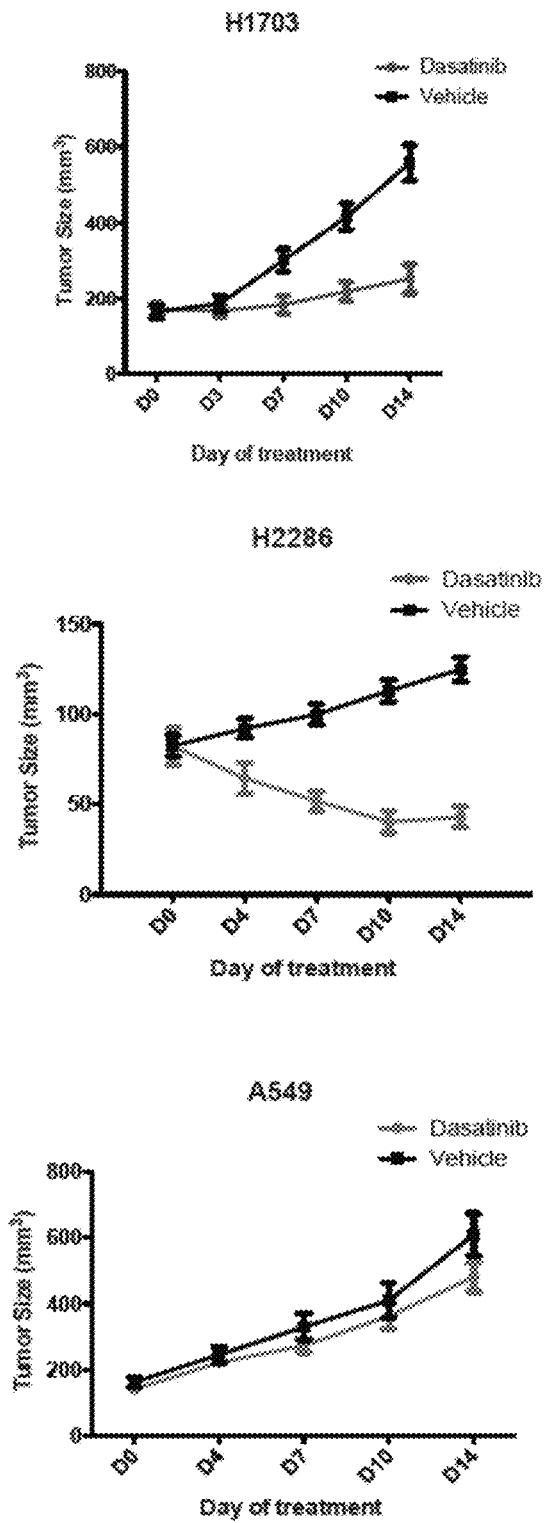
FIG. 3: Xenografts of squamous lung cancer cell lines demonstrate anti-tumor effects of dasatinib in vivo. Athymic nu/nu mice were injected subcutaneously with A549, NCI-H1703, HCC-366 and NCI-H2286 cells (n=10) and treated with dasatinib or vehicle for two weeks following tumor formation. Depicted are measurements of tumor size in mice from each cohort. Tumors did not form in the mice injected with HCC-366 and these mice could not be analyzed further.

To analyze the effects of dasatinib treatment in a somewhat more physiological setting, xenograft studies were performed in athymic nude mice in which cohorts of mice were injected with NCI-H2286, HCC-366, NCI-H1703 and A549 cells. HCC-366 cells did not form tumors in the mice and could not be analyzed further. Following tumor formation of the three tested lines mice were treated with dasatinib at 50 mg/kg by oral gavage for two weeks or vehicle control. Dasatinib treatment led to a decrease in tumor size in the NCI-H1703 and NCI-H2286 lines but not in A549, consistent with the in vitro results (FIG. 3).

Example 5

Figure 4A:
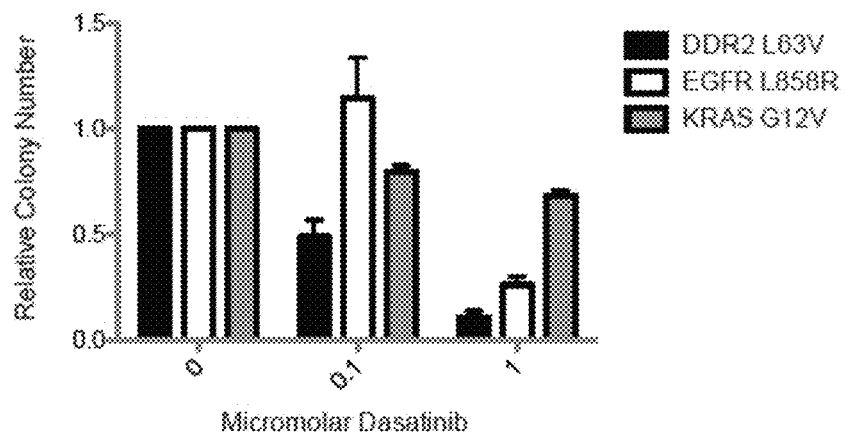
FIGS. 4a-d: Ectopic expression of DDR2 mutants leads to cellular transformation which can be blocked by dasatinib or combination tyrosine kinase inhibitor treatment. (a) Results from soft agar assay in which 3T3 fibroblasts expressing the L63V DDR2 mutation, the L858R EGFR mutation or the KRAS G12V mutation were plated in soft agar in the presence of various concentrations of dasatinib. Colony number of six independent samples with standard errors is shown. (b) Proliferation at four days of Ba/F3 cells expressing vector only or one of six DDR2 mutations shown in cells grown in the presence of dasatinib. For the vector control cells are grown in the presence of IL-3 to maintain viability and in the case of the DDR2 mutants all cells are IL-3 independent and cultured in the absence of IL-3. Proliferation is shown relative to untreated cells at the same time point for triplicate samples with standard errors. (c) Proliferation of Ba/F3 cells expressing DDR2 L63V co-cultured with 50 nM of nilotinib, AP24534 or dasatinib with or without 500 nM AZD0530. Proliferation is relative to untreated cells grown in parallel. (d) Immunoblots of DDR2 L63V transformed Ba/F3 cells treated for two days with the depicted concentrations of AZD0530 (AZD) in addition to 50 nM nilotinib (N), AP24534 (AP) or dasatinib (D). The first lane is an untreated sample. Shown are immunoblots probed with antibodies against phospho-Src Y416, phospho-STAT5 Y694, FLAG-DDR2 and actin.
Figure 4B:
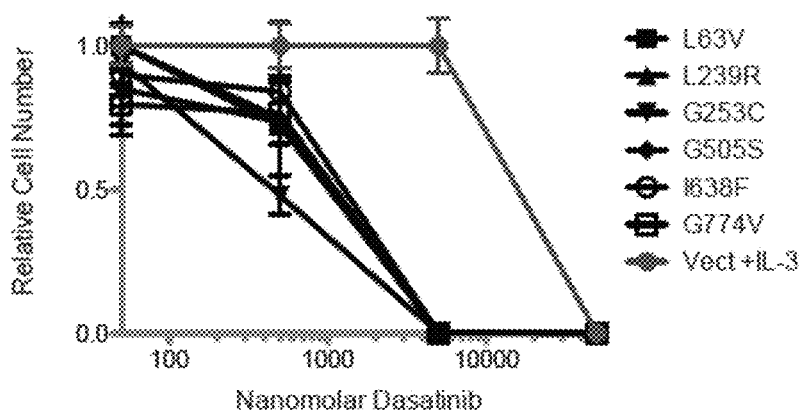
Figure 4C:
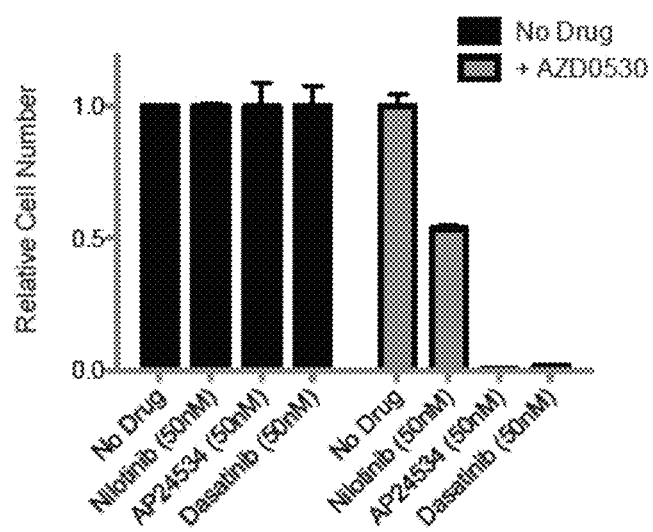
Figure 4D:
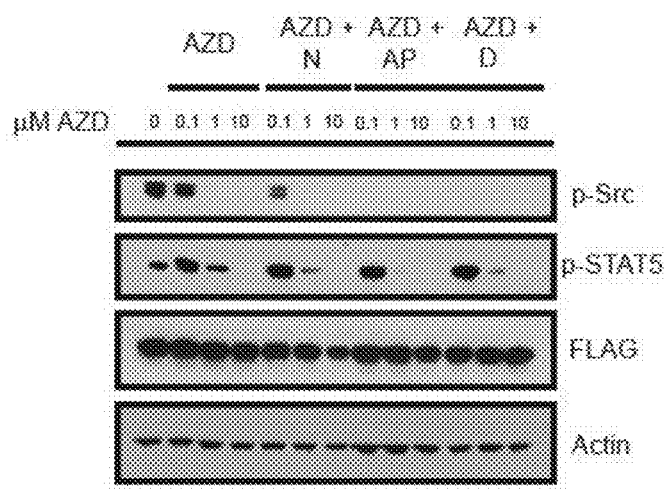
Figure 4E:
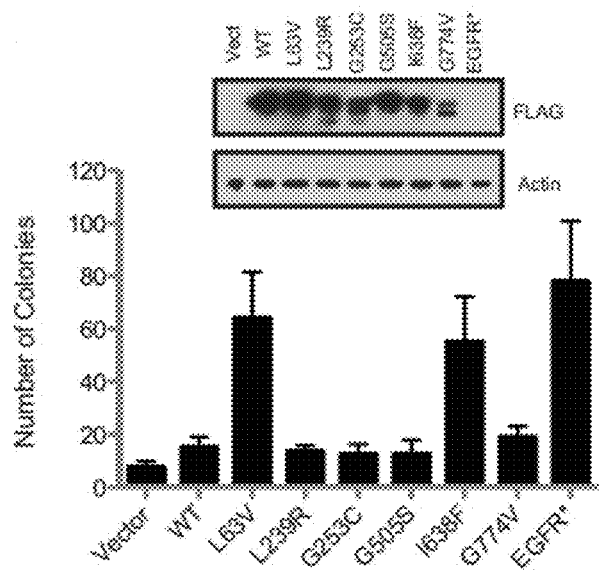
FIGS. 4e-h: Ectopic expression of DDR2 leads to cellular transformation which is sensitive to AP24534 treatment. (e) Colony formation in soft agar of NIH-3T3 fibroblasts stably expressing the vector alone or wild-type or various mutant forms of DDR2. Colony numbers with standard errors are shown for six independent samples. Expression of FLAG-tagged DDR2 by immunoblotting of the cells used in the transformation assay is shown in the inset and actin serves as a loading control. 3T3 fibroblasts expressing the activating L858R mutation of EGFR (EGFR*) are used as a positive control. (f) Time to IL-3 independence is shown for Ba/F3 cells stably expressing vector alone or wild-type or mutant forms of DDR2. Expression level of the transgenes and KD DDR2 (K608E) is shown as well as actin. The KD DDR2 was probed on a separate membrane which is indicated by the separation bar. (g) Proliferation at four days of Ba/F3 cells expressing vector only or one of six DDR2 mutations is shown in cells grown in the presence of imatinib. For the vector control the cells are grown in the presence of IL-3 to maintain viability and in the case of the DDR2 mutants all cells are IL-3 independent and cultured in the absence of IL-3. Proliferation is shown relative to untreated cells at the same time point for triplicate samples with standard errors. (h) Experiment as above with AP24534.

DDR2 Mutations are Oncogenic and DDR2-Driven Transformation is Dasatinib-Sensitive Next, the ability of DDR2 mutations to confer an oncogenic gain-of-function phenotype was examined. Ectopic expression of a subset of the DDR2 mutants identified in our primary and secondary screens (n=2/6) promoted the formation of colonies in soft agar of NIH-3T3 cells (FIG. 4e). Colony formation was greatest in the L63V and I638F mutants at a level comparable to that driven by expression of the gain-of-function L858R mutation in EGFR and modest in the remainder of the genotypes. Colony formation could be inhibited with a single application of dasatinib at the time of plating in the case of the L63V mutant, the mutant which reproducibly formed the most colonies in our assay (FIG. 4a). Dasatinib treatment also inhibited the colony formation of NIH-3T3 cells expressing the L858R mutation in EGFR, consistent with previous reports, and did so to a lesser extent in NIH-3T3 cells stably expressing the activating G12V KRAS mutation (FIG. 4a) (32, 37).

Figure 4F:
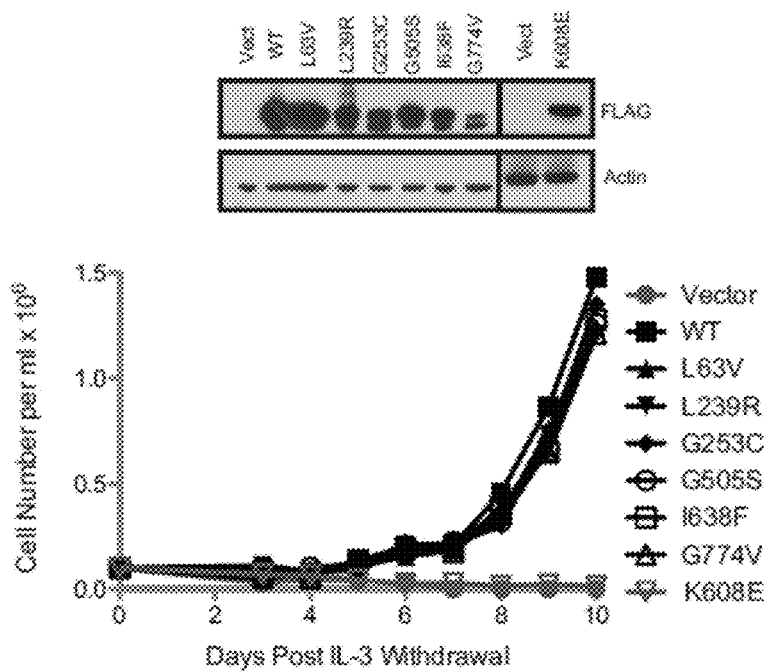
Figure 4G:
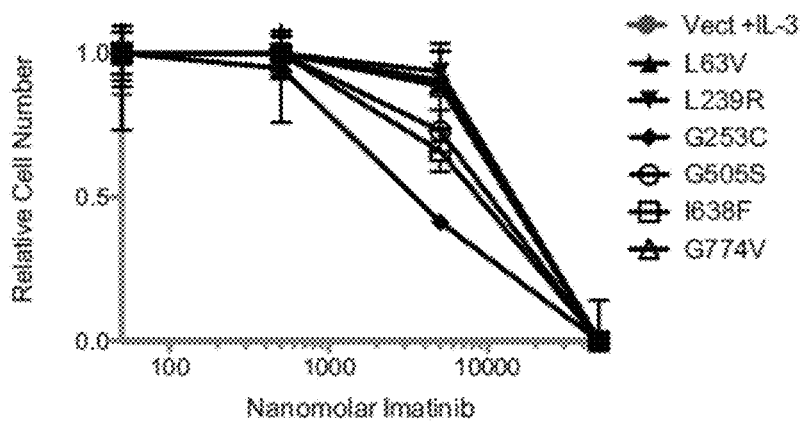
Figure 4H:
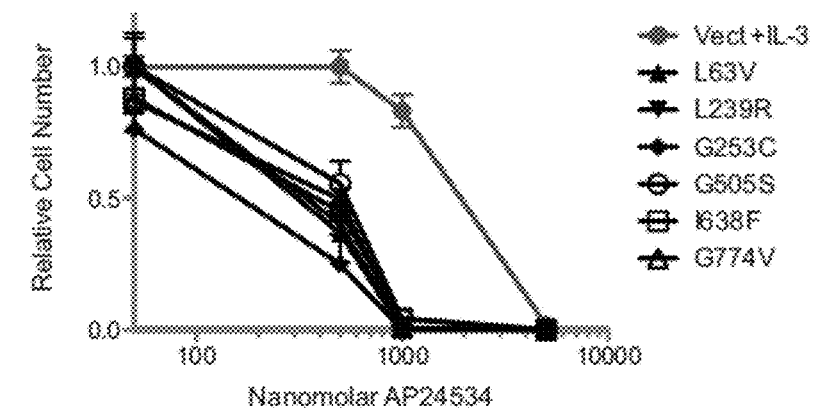
Figure 4I:
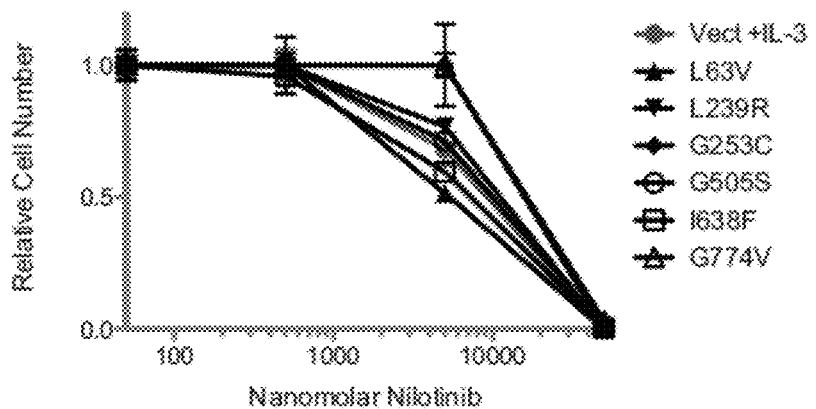
FIGS. 4*i-l*: DDR2-transformed Ba/F3 cells maintain Src and STAT5 phosphorylation and treatment of Ba/F3 cells expressing mutant forms of DDR2 with nilotinib or AZD0530 results in minimal toxicity. (i) Proliferation at four days of Ba/F3 cells expressing vector only or one of six DDR2 mutations is shown in cells grown in the presence of nilotinib. For the vector control the cells are grown in the presence of IL-3 to maintain viability and in the case of the DDR2 mutants all cells are IL-3 independent and cultured in the absence of IL-3. Proliferation is shown relative to untreated cells at the same time point for triplicate samples with standard errors. (j) Immunoblots showing the levels of phospho-Src (Y416), phospho-STAT5 (Y694) and actin in Ba/F3 cells expressing mutant forms of DDR2 or the vector alone from the cell lines shown in Supplementary FIG. 3*b*. All DDR2 mutant lines are grown in the absence of IL-3 and the vector is shown in the presence and absence of IL-3. (k) Experiment as above with Ba/F3 cells grown in the presence of AZD0530. (l) Immunoblots of DDR2 L63V transformed Ba/F3 cells treated for two days with the depicted concentrations of AZD0530, nilotinib (N), AP24534 (AP) or dasatinib (D). The first lane is an untreated sample. Shown are immunoblots probed with antibodies against phospho-Src, phospho-STAT5, FLAG-DDR2 and actin.

As the observed gain-of-function phenotype was modest for many of the DDR2 mutants in NIH-3T3 cells, the transforming potential of DDR2 was evaluated in the interleukin-3 (IL-3)-dependent hematopoietic cell line Ba/F3. Ectopic expression of all six DDR2 mutants identified in the primary and secondary screens led to IL-3-independent growth of Ba/F3 cells as did high levels of expression of wild-type DDR2 and no differences were observed in the time to transformation or the rate of IL-3 independent proliferation (FIG. 4f). A kinase-dead DDR2 transgene (K608E) did not support the IL-3-independent growth of Ba/F3 cells (FIG. 4f). While culture with the less potent DDR2 inhibitor imatinib did not lead to significant killing of Ba/F3 cells expressing DDR2 mutations as compared to cells grown in the presence of IL-3, culture with dasatinib led to cell death in all cell lines expressing DDR2 mutants with a mean calculated $IC_{50}$ of 680 nM for the mutants and 30 mM for the control (FIGS. 4b and 4g). The third-generation BCR-Abl inhibitor AP24534 was also effective in killing the IL-3-independent Ba/F3 cells expressing mutant forms of DDR2, suggesting that this class of drugs may be effective against DDR2-driven neoplasms while the second generation BCR-Abl inhibitor nilotinib demonstrated modest activity against the DDR2-transformed Ba/F3 cells (FIGS. 4h and 4i). Survival of Ba/F3 cells in the absence of IL-3 was associated with maintenance of STAT5 phosphorylation as has been previously shown (FIG. 4j) (38).

Example 6

Figure 4J:
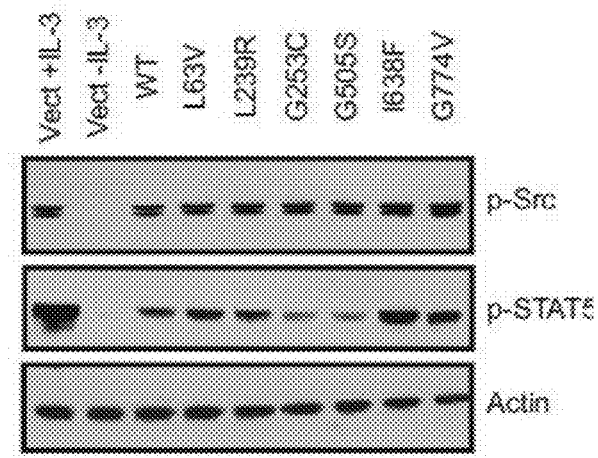
Figure 4K:
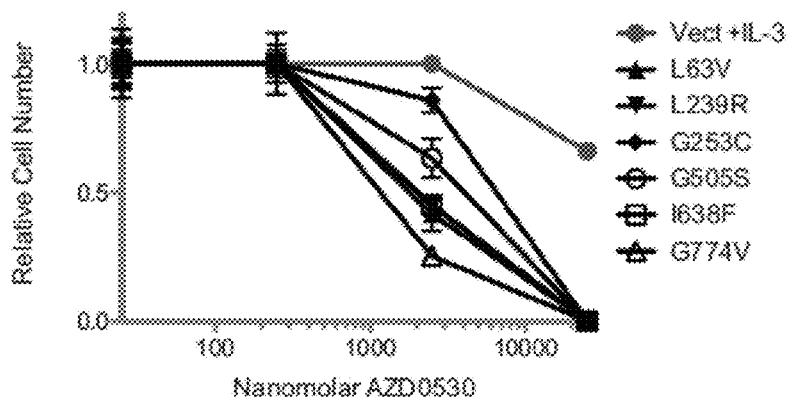
Figure 4L:
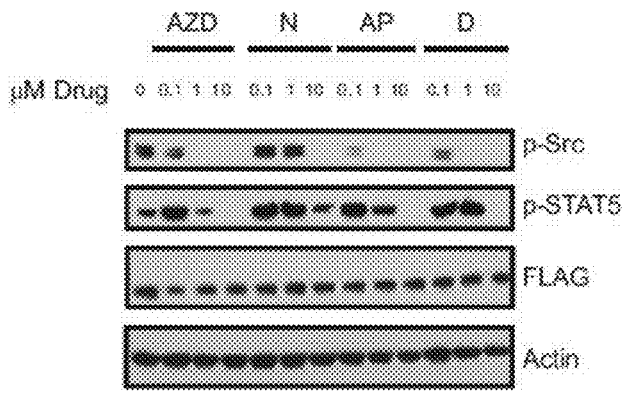
Figure 4M:
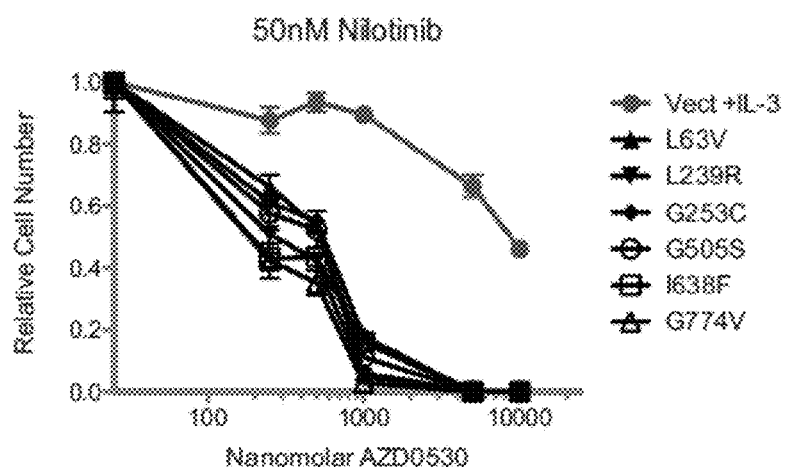
FIGS. 4*m-o*: Combination treatment with nilotinib, AP24534 or dasatinib and AZD0530 leads to increased killing of DDR2 transformed Ba/F3 cells. (m) Proliferation at four days of Ba/F3 cells expressing vector only or one of six DDR2 mutations is shown in cells grown in the presence of a fixed concentration 4 of nilotinib and the depicted amounts of AZD0530. For the vector control the cells are grown in the presence of IL-3 to maintain viability and in the case of the DDR2 mutants all cells are IL-3 independent and cultured in the absence of IL-3. Proliferation is shown relative to untreated cells at the same time point for triplicate samples with standard errors. (n) Experiment performed as above with AP24534 and AZD0530. (o) Experiment performed as above with dasatinib and AZD0530.
Figure 4N:
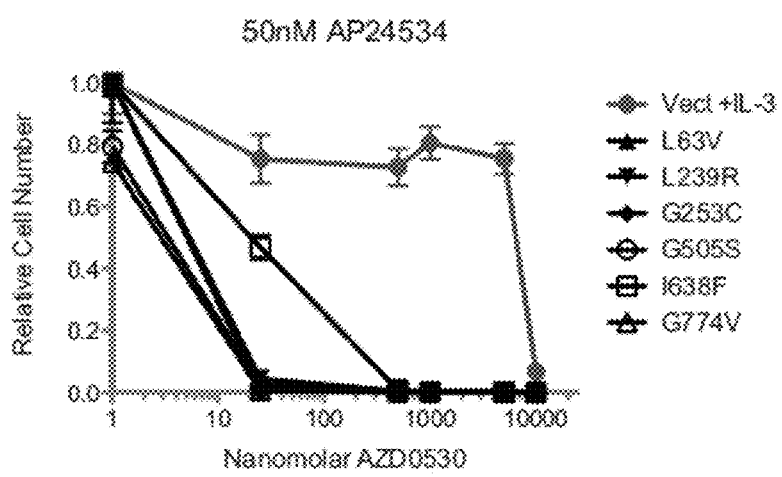
Figure 4O:
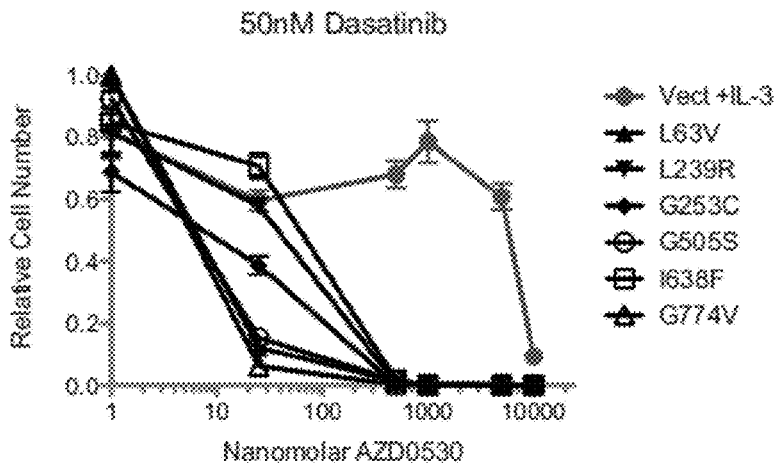

DDR2 Transformed Cell Lines Maintain Src Phosphorylation and are Especially Sensitive to Dual Inhibition of DDR2 and Src Given that the type I kinase inhibitor dasatinib was more potent in DDR2-transformed Ba/F3 cells than the more target-specific type II inhibitors nilotinib and imatinib, whether the potency of dasatinib in this system might be due to effects of dasatinib on other kinases in addition to DDR2 was evaluated. DDR2 has previously been shown to require Src for maximal kinase activity (16) and levels of phosphorylated Src were maintained in Ba/F3 cells expressing DDR2 mutants in the absence of IL-3 (FIG. 4j). To test whether the ability of DDR2 mutations to confer IL-3-independent proliferation in Ba/F3 cells might depend on both DDR2 and Src activity, Ba/F3 cells expressing DDR2 were treated with AZD0530, a highly selective Src-family kinase inhibitor which displays minimal activity against DDR2 as compared to the other inhibitors described in this manuscript (in vitro $K_d$ 291 nM, Table 1) (39). Similar to nilotinib treatment, AZD0530 had a modest effect on the proliferation of the IL-3-independent DDR2-expressing Ba/F3 cells (FIGS. 4i and 4k). However, when Ba/F3 cells expressing the L63V DDR2 mutation were grown in 50 nM nilotinib, a concentration associated with little effect on proliferation of wild-type Ba/F3 cells or Ba/F3 cells expressing DDR2 mutations (FIG. 4i), the addition of AZD0530 led to a marked reduction in proliferation of Ba/F3 cells expressing DDR2 L63V, suggesting that the coordinated activity of DDR2 and Src-family kinases may be required for the ability of DDR2 mutated Ba/F3 cells to grow in the absence of IL-3 and thereby providing a possible explanation for the potency of dasatinib in this system (FIGS. 4c and 4m). A similar additive effect of AZD0530 was observed when the Ba/F3 cells were co-treated with AZD0530 and 50 nM of either AP24534 or dasatinib (FIG. 4c for L63V; for a more detailed version of this experiment including additional DDR2 mutants see FIGS. 4m-o). AZD0530 reduced Src and STAT5 phosphorylation in a dose-dependent fashion in the DDR2 L63V-expressing Ba/F3 cells when used as a single agent or in combination with nilotinib, AP24534 or dasatinib (FIGS. 4d and 4l).

Example 7

Figure 5A:
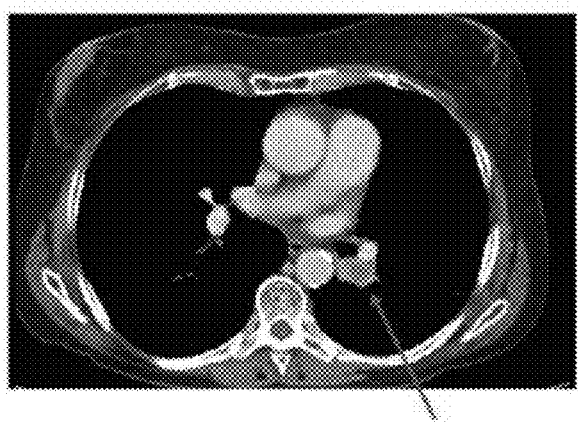
FIGS. 5*a-b*: Radiographic response of a patient with a S768R DDR2 mutation treated with dasatinib plus erlotinib. (a) CT scan images shown from a lung SCC patient who was treated with chemotherapy and later with dasatinib plus erlotinib. Serial CT scans are shown at the time of initiation of chemotherapy, initiation of study treatment with dasatinib and erlotinib and following two months of treatment with dasatinib plus erlotinib. (b) Top panel: Tumor dimension measurements from the subject above starting four months prior to chemotherapy treatment and extending to the time at which combination therapy with dasatinib and erlotinib was discontinued. Bottom panel: Bar graph depicting measured tumor volume by RECIST criteria of the subject prior to chemotherapy, following chemotherapy and following two months of dasatinib plus erlotinib therapy.
Figure 5A:
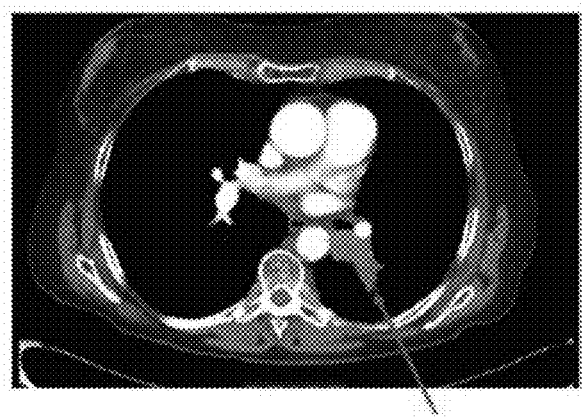
Figure 5A:
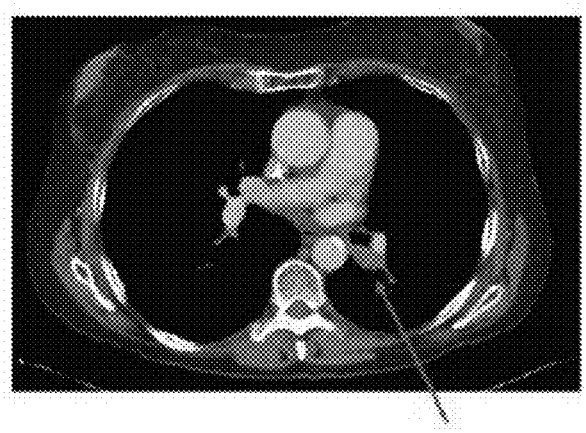
Figure 5B:
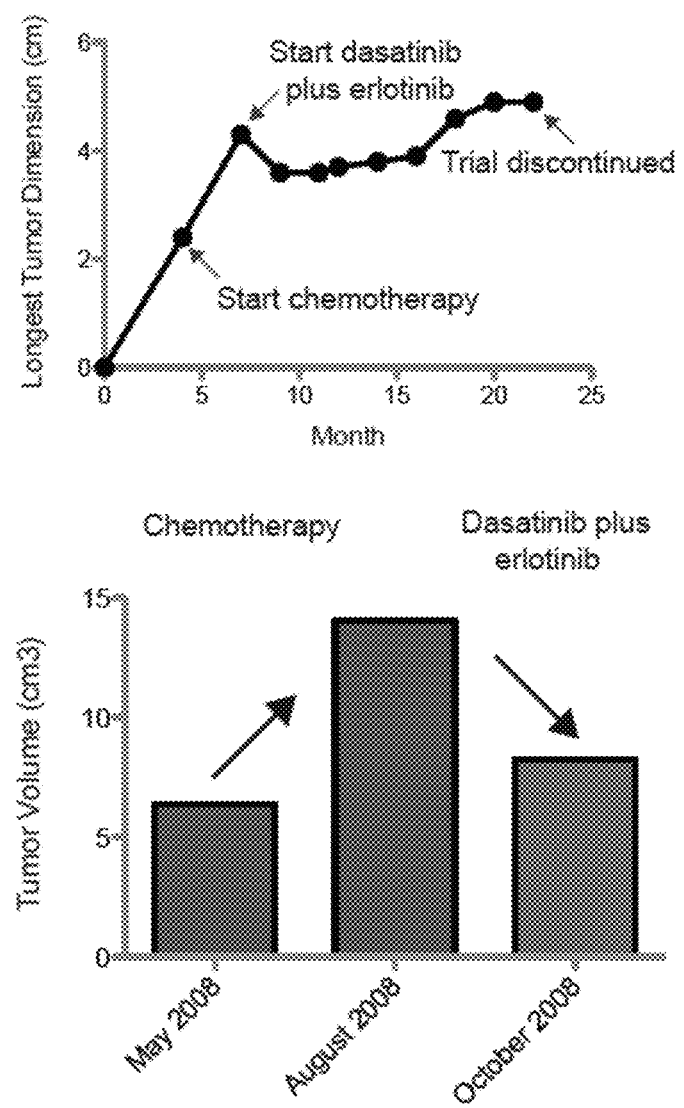

Observation of a DDR2 Kinase Domain Mutation in a Clinical Trial Subject with a Radiographic Response to Combination Therapy with Dasatinib and Erlotinib Two recent early-phase clinical trials of dasatinib have been reported in which subjects with advanced stage lung cancer were treated with either dasatinib or a combination of dasatinib and erlotinib (29, 40). One of seven subjects with a squamous cell lung cancer exhibited a significant shrinkage in tumor size while undergoing therapy with a combination of dasatinib and erlotinib, and unlike the other subject on study with lung adenocarcinoma who exhibited a response to treatment, there was no evidence of EGFR mutation in the subject with squamous cell lung cancer. The patient was a 59 year old Caucasian woman with a ⅓ pack per day smoking history for 38 years who quit one year before her diagnosis of lung cancer. She was found to have a left lower lobe stage I (T2N0M0) squamous cell lung cancer and received primary treatment with weekly carboplatin and paclitaxel with concomitant 70 Gy of radiation resulting in a complete response. However, approximately one year later she developed progression of disease within the radiation field and treatment was initiated with s standard dose carboplatin and paclitaxel without response. She then began combination dasatinib and erlotinib therapy on protocol. A restaging CT scan after nearly 2 months indicated tumor shrinkage and the patient experienced improved symptoms (resolved dyspnea and cough) (FIGS. 5A and 5B). She remained on treatment for 14 months until therapy had to be discontinued secondary to treatment-induced airspace disease and pleural effusions.

Directed sequencing of DDR2 was performed in a pretreatment tumor specimen derived from this individual and a novel DDR2 kinase domain mutation, S768R, was identified that was present in 844 of 3020 (28%) of reads obtained by 454 sequencing and independently verified by Sanger sequencing. The mutation could not be verified as somatic as no normal DNA was available for this individual who is deceased. There were no other SCC subjects who responded to therapy on this study or a subsequent study of dasatinib alone (n=13 total) to further explore this correlation.

Three-dimensional modeling of the S768R mutation in the context of the DDR2 kinase domain was performed. A structural model of the kinase domain of DDR2 (residues 545-854) was generated based on the crystal structure of the Abl kinase domain in the active (DFG-in) conformation (PDB code: 3DK6) in complex with a small molecule inhibitor. Dasatinib was modeled into the ATP-binding site of DDR2 based on the crystal structure of dasatinib in complex with cSrc (PDB code: 3G5D). The proposed binding mode showed the inhibitor core within hydrogen bonding distance to the backbone of the hinge region of the kinase domain. The terminal ethanol-piperazine was solvent exposed. The activating mutation Ser768Arg was found at the N-terminal end of a helix below the 5 activation loop. The structural model indicated that the side chain of Ser768 in wild type DDR2 likely resides in a packed environment flanked by Glu213 and Phe220. The extra charge and steric bulk of an Arg at position 768 in mutant DDR2 is likely to introduce structural changes in this region which could potentially alter the kinase activity and/or regulatory mechanisms of DDR2. These results suggest that the S768R substitution is likely to alter the kinase activity of DDR2.

REFERENCES

1. Lennes I T, Lynch T J. Quality indicators in cancer care: development and implementation for improved health outcomes in non-small-cell lung cancer. Clin Lung Cancer. 2009; 10(5):341-6.
2. West H, Harpole D, Travis W. Histologic considerations for individualized systemic therapy approaches for the management of non-small cell lung cancer. Chest. 2009; 136(4):1112-8.
3. Pao W, Miller V A, Politi K A, Riely G J, Somwar R, Zakowski M F, et al. Acquired resistance of lung adenocarcinomas to gefitinib or erlotinib is associated with a second mutation in the EGFR kinase domain. PLoS Med. 2005; 2(3):e73. PMCID: 549606.
4. Paez J G, Janne P A, Lee J C, Tracy S, Greulich H, Gabriel S, et al. EGFR mutations in lung cancer: correlation with clinical response to gefitinib therapy. Science. 2004; 304 (5676): 1497-500.
5. Lynch T J, Bell D W, Sordella R, Gurubhagavatula S, Okimoto R A, Brannigan B W, et al. Activating mutations in the epidermal growth factor receptor underlying responsiveness of non-small-cell lung cancer to gefitinib. N Engl J Med. 2004; 350(21):2129-39.
6. Shigematsu H, Lin L, Takahashi T, Nomura M, Suzuki M, Wistuba, I I, et al. Clinical and biological features associated with epidermal growth factor receptor gene mutations in lung cancers. J Natl Cancer Inst. 2005; 97(5): 339-46.
7. Sasaki T, Rodig S J, Chirieac L R, Janne P A. The biology and treatment of EML4-ALK non-small cell lung cancer. Eur J Cancer. 2010.
8. Hammerman P S, Janne P A, Johnson B E. Resistance to Epidermal Growth Factor Receptor Tyrosine Kinase Inhibitors in Non-Small Cell Lung Cancer. Clin Cancer Res. 2009; 15(24):7502-9.
9. Mok T S, Wu Y L, Thongprasert S, Yang C H, Chu D T, Saijo N, et al. Gefitinib or carboplatin-paclitaxel in pulmonary adenocarcinoma. N Engl J Med. 2009; 361(10): 947-57.
10. Shaw A T, Yeap B Y, Mino-Kenudson M, Digumarthy S R, Costa D B, Heist R S, et al. Clinical features and outcome of patients with non-small-cell lung cancer who harbor EML4-ALK. J Clin Oncol. 2009; 27(26):4247-53. PMCID: 2744268.
11. Weiss J, Sos M L, Seidel D, Peifer M, Zander T, Heuckmann J M, et al. Frequent and focal FGFR1 amplification associates with therapeutically tractable FGFR1 dependency in squamous cell lung cancer. Sci Transl Med. 2010; 2(62):62ra93.
12. Vogel W, Gish G D, Alves F, Pawson T. The discoidin domain receptor tyrosine kinases are activated by collagen. Mol Cell. 1997; 1(1):13-23.
13. Vogel W. Discoidin domain receptors: structural relations and functional implications. FASEB J. 1999; 13 Suppl:S77-82.
14. Shrivastava A, Radziejewski C, Campbell E, Kovac L, McGlynn M, Ryan T E, et al. An orphan receptor tyrosine kinase family whose members serve as nonintegrin collagen receptors. Mol Cell. 1997; 1(1):25-34.
15. Leitinger B. Molecular analysis of collagen binding by the human discoidin domain receptors, DDR1 and DDR2. Identification of collagen binding sites in DDR2. J Biol Chem. 2003; 278(19):16761-9.
16. Ikeda K, Wang L H, Torres R, Zhao H, Olaso E, Eng F J, et al. Discoidin domain receptor 2 interacts with Src and Shc following its activation by type I collagen. J Biol Chem. 2002; 277(21):19206-12.
17. Olaso E, Labrador J P, Wang L, Ikeda K, Eng F J, Klein R, et al. Discoidin domain receptor 2 regulates fibroblast proliferation and migration through the extracellular matrix in association with transcriptional activation of matrix metalloproteinase-2. J Biol Chem. 2002; 277(5): 3606-13.
18. Labrador J P, Azcoitia V, Tuckermann J, Lin C, Olaso E, Manes S, et al. The collagen receptor DDR2 regulates proliferation and its elimination leads to dwarfism. EMBO Rep. 2001; 2(5):446-52. PMCID: 1083888.
19. Ford C E, Lau S K, Zhu C Q, Andersson T, Tsao M S, Vogel W F. Expression and mutation analysis of the 19. discoidin domain receptors 1 and 2 in non-small cell lung carcinoma. Br J Cancer. 2007; 96(5):808-14. PMCID: 2360060.
20. Davies H, Hunter C, Smith R, Stephens P, Greenman C, Bignell G, et al. Somatic mutations of the protein kinase gene family in human lung cancer. Cancer Res. 2005; 65(17):7591-5.
21. Day E, Waters B, Spiegel K, Alnadaf T, Manley P W, Buchdunger E, et al. Inhibition of collagen-induced discoidin domain receptor 1 and 2 activation by imatinib, nilotinib and dasatinib. Eur J Pharmacol. 2008; 599(1-3): 44-53.
22. Raponi M, Zhang Y, Yu J, Chen G, Lee G, Taylor J M, et al. Gene expression signatures for predicting prognosis of squamous cell and adenocarcinomas of the lung. Cancer Res. 2006; 66(15):7466-72.
23. Bass A J, Watanabe H, Mermel C H, Yu S, Perner S, Verhaak R G, et al. SOX2 is an amplified lineage-survival oncogene in lung and esophageal squamous cell carcinomas. Nat Genet. 2009; 41(11):1238-42. PMCID: 2783775.
24. Beroukhim R, Mermel C H, Porter D, Wei G, Raychaudhuri S, Donovan J, et al. The landscape of somatic copy-number alteration across human cancers. Nature. 2010; 463(7283):899-905. PMCID: 2826709.
25. Stegmeier F, Warmuth M, Sellers W R, Dorsch M. Targeted cancer therapies in the twenty-first century: lessons from imatinib. Clin Pharmacol Ther. 2010; 87(5): 543-52.
26. Manley P W, Drueckes P, Fendrich G, Furet P, Liebetanz J, Martiny-Baron G, et al. Extended kinase profile and properties of the protein kinase inhibitor nilotinib. Biochim Biophys Acta. 2010; 1804(3):445-53.
27. Li J, Rix U, Fang B, Bai Y, Edwards A, Colinge J, et al. A chemical and phosphoproteomic characterization of dasatinib action in lung cancer. Nat Chem Biol. 2010; 6(4):291-9. PMCID: 2842457.
28. Karaman M W, Herrgard S, Treiber D K, Gallant P, Atteridge C E, Campbell B T, et al. A quantitative analysis of kinase inhibitor selectivity. Nat Biotechnol. 2008; 26(1):127-32.
29. Haura E B, Tanvetyanon T, Chiappori A, Williams C, Simon G, Antonia S, et al. Phase I/II study of the Src inhibitor dasatinib in combination with erlotinib in advanced non-small-cell lung cancer. J Clin Oncol. 2010; 28(8):1387-94.
30. Tonon G, Wong K K, Maulik G, Brennan C, Feng B, Zhang Y, et al. High-resolution genomic profiles of human lung cancer. Proc Natl Acad Sci USA. 2005; 102(27): 9625-30. PMCID: 1160520.
31. Ramos A H, Dutt A, Mermel C, Perner S, Cho J, Lafargue C J, et al. Amplification of chromosomal segment 4q12 in non-small cell lung cancer. Cancer Biol Ther. 2009; 8(21):2042-50. PMCID: 2833355.
32. Sos M L, Michel K, Zander T, Weiss J, Frommolt P, Peifer M, et al. Predicting drug susceptibility of non-small cell lung cancers based on genetic lesions. J Clin Invest. 2009; 119(6):1727-40. PMCID: 2689116.
33. Du J, Bernasconi P, Clauser K R, Mani D R, Finn S P, Beroukhim R, et al. Bead-based profiling of tyrosine kinase phosphorylation identifies SRC as a potential target for glioblastoma therapy. Nat Biotechnol. 2009; 27(1): 77-83.
34. Quintas-Cardama A, Kantarjian H, Cortes J. Imatinib and beyond—exploring the full potential of targeted therapy for CML. Nat Rev Clin Oncol. 2009; 6(9):535-43.
35. Kim L C, Rix U, Haura E B. Dasatinib in solid tumors. Expert Opin Investig Drugs. 2010; 19(3):415-25.
36. O'Hare T, Shakespeare W C, Zhu X, Eide C A, Rivera V M, Wang F, et al. AP24534, a pan-BCR-ABL inhibitor for chronic myeloid leukemia, potently inhibits the T315I mutant and overcomes mutation-based resistance. Cancer Cell. 2009; 16(5):401-12. PMCID: 2804470.
37. Song L, Morris M, Bagui T, Lee F Y, Jove R, Haura E B. Dasatinib (BMS-354825) selectively induces apoptosis in lung cancer cells dependent on epidermal growth factor receptor signaling for survival. Cancer Res. 2006; 66(11): 5542-8.
38. Nosaka T, Kawashima T, Misawa K, Ikuta K, Mui A L, Kitamura T. STAT5 as a molecular regulator of proliferation, differentiation and apoptosis in hematopoietic cells. EMBO J. 1999; 18(17):4754-65. PMCID: 1171548.
39. Hennequin L F, Ballard P, Boyle F T, Delouvrie B, Ellston R P, Halsall C T, et al. Novel 4-anilinoquinazolines with C-6 carbon-linked side chains: synthesis and structure-activity relationship of a series of potent, orally active, EGF receptor tyrosine kinase inhibitors. Bioorg Med Chem Lett. 2006; 16(10):2672-6.
40. Johnson F M, Bekele B N, Feng L, Wistuba I, Tang X M, Tran H T, et al. Phase II study of dasatinib in patients with advanced non-small-cell lung cancer. J Clin Oncol. 2010; 28(30):4609-15. PMCID: 2974341.
41. McDermott U, Iafrate A J, Gray N S, Shioda T, Classon M, Maheswaran S, et al. Genomic alterations of anaplastic lymphoma kinase may sensitize tumors to anaplastic lymphoma kinase inhibitors. Cancer Res. 2008; 68(9): 3389-95.
42. Kan Z, Jaiswal B S, Stinson J, Janakiraman V, Bhatt D, Stern H M, et al. Diverse somatic mutation patterns and pathway alterations in human cancers. Nature. 2010; 466(7308):869-73.
43. Available on the internet at statpages.org/proppowr.html
44. Bargal R, Cormier-Daire V, Ben-Neriah Z, Le Merrer M, Sosna J, Melki J, et al. Mutations in DDR2 gene cause SMED with short limbs and abnormal calcifications. Am J Hum Genet. 2009; 84(1):80-4. PMCID: 2668047.
45. Ali B R, Xu H, Akawi N A, John A, Karuvantevida N S, Langer R, et al. Trafficking defects and loss of ligand binding are the underlying causes of all reported DDR2 missense mutations found in SMED-S L patients. Hum Mol Genet. 2010; 19(11):2239-50. PMCID: 2865377.
46. Moffat J, Grueneberg D A, Yang X, Kim S Y, Kloepfer A M, Hinkle G, et al. A lentiviral RNAi library for human and mouse genes applied to an arrayed viral high-content screen. Cell. 2006; 124(6):1283-98.
47. Luo B, Cheung H W, Subramanian A, Sharifnia T, Okamoto M, Yang X, et al. Highly parallel identification of essential genes in cancer cells. Proc Natl Acad Sci USA. 2008; 105(51):20380-5. PMCID: 2629277.
48. Available on the internet at broadinstitute.org/rnai/public/resources/protocols

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject diagnosed with squamous cell carcinoma (SCC) of the lung, the method comprising:
   performing an assay to determine the identity of the nucleotides at codon 768 of discoidin domain receptor 2 (DDR2) gene in a sample comprising nucleated cells from the SCC in the subject;
   determining an expected amino acid translation of the determined DDR2 sequence;
   comparing the expected amino acid translation with a reference amino acid, wherein the reference amino acid is a serine;
   detecting the presence of an amino acid variation relative to the reference amino acid, wherein the amino acid variation is S768R; and
   administering a treatment comprising dasatinib to the subject having a S768R variation in DDR2 gene.

2. The method of claim 1, wherein performing an assay to determine the identity of the nucleotides at codon 768 comprises using microarray analysis.

3. The method of claim 1, wherein performing an assay to determine the identity of the nucleotides at codon 768 comprises using a nucleic acid probe that specifically hybridizes with a sequence encoding a S768R mutation.

4. A method of treating a human subject diagnosed with squamous cell carcinoma (SCC) of the lung, the method comprising:
   performing an assay to determine the identity of the nucleotides at codon 768 of discoidin domain receptor 2 (DDR2) gene in a sample comprising nucleated cells from the SCC in the subject;

determining an expected amino acid translation of the determined DDR2 sequence;

comparing the expected amino acid translation with a reference amino acid, wherein the reference amino acid is a serine;

detecting the presence of an amino acid variation relative to the reference amino acid, wherein the amino acid variation is S768R; and administering a treatment comprising nilotinib to the subject having a S768R variation in DDR2 gene.

5. The method of claim 4, wherein performing an assay to determine the identity of the nucleotides at codon 768 comprises using microarray analysis.

6. The method of claim 4, wherein performing an assay to determine the identity of the nucleotides at codon 768 comprises using a nucleic acid probe that specifically hybridizes with a sequence encoding a S768R mutation.

7. A method of treating a human subject diagnosed with squamous cell carcinoma (SCC) of the lung, the method comprising:

performing an assay to determine the identity of the nucleotides at codon 768 of discoidin domain receptor 2 (DDR2) gene in a sample comprising nucleated cells from the SCC in the subject;

comparing the expected amino acid translation with a reference amino acid, wherein the reference amino acid is a serine;

determining an expected amino acid translation of the determined DDR2 sequence;

comparing the expected amino acid translation with a reference amino acid, wherein the reference amino acid is a serine;

detecting the presence of an amino acid variation relative to the reference amino acid, wherein the amino acid variation is S768R; and administering a treatment comprising imatinib to the subject having a S768R variation in DDR2 gene.

8. The method of claim 7, wherein performing an assay to determine the identity of the nucleotides at codon 768 comprises using microarray analysis.

9. The method of claim 7, wherein performing an assay to determine the identity of the nucleotides at codon 768 comprises using a nucleic acid probe that specifically hybridizes with a sequence encoding a S768R mutation.

10. A method of treating a human subject diagnosed with squamous cell carcinoma (SCC) of the lung, the method comprising:

performing an assay to determine the identity of the nucleotides at codon 768 of discoidin domain receptor 2 (DDR2) gene in a sample comprising nucleated cells from the SCC in the subject;

determining an expected amino acid translation of the determined DDR2 sequence; comparing the expected amino acid translation with a reference amino acid, wherein the reference amino acid is a serine;

detecting the presence of an amino acid variation relative to the reference amino acid, wherein the amino acid variation is S768R; and administering a treatment comprising ponatinib to the subject having a S768R variation in the DDR2 gene.

11. The method of claim 10, wherein performing an assay to determine the identity of the nucleotides at codon 768 comprises using microarray analysis.

12. The method of claim 10, wherein performing an assay to determine the identity of the nucleotides at codon 768 comprises using a nucleic acid probe that specifically hybridizes with a sequence encoding a S768R mutation.

13. A method of treating a human subject diagnosed with squamous cell carcinoma (SCC) of the lung, the method comprising:

providing a sample comprising nucleated cells from the SCC in the subject;

contacting the sample with a nucleic acid probe that specifically hybridizes with a sequence encoding a S768R mutation of discoidin domain receptor 2 (DDR2) gene under high stringency;

detecting the presence of S768R mutation in DDR2 by hybridization of the nucleic acid probe to the DDR2 gene; and administering a treatment comprising dasatinib, nilotinib, imatinib, or ponatinib to the subject having a S768R mutation in the DDR2 gene.

14. The method of claim 13, wherein dasatinib is administered.

15. The method of claim 13, wherein nilotinib is administered.

16. The method of claim 13, wherein imatinib is administered.

17. The method of claim 13, wherein ponatinib is administered.

18. A method of treating a human subject diagnosed with squamous cell carcinoma (SCC) of the lung, the method comprising:

performing an assay to determine the identity of the nucleotides at codon 768 of discoidin domain receptor 2 (DDR2) gene in a sample comprising nucleated cells from the SCC of the subject;

determining an expected amino acid translation of the identified nucleotides at codon 768;

comparing the expected amino acid translation with a reference amino acid, wherein the reference amino acid is serine;

detecting the presence of an amino acid variation relative to the reference amino acid, wherein the amino acid variation is S768R; and administering a treatment comprising a tyrosine kinase inhibitor (TKI) to the subject having a S768R variation in the DDR2 gene.

19. The method of claim 18, wherein performing an assay to determine the identity of the nucleotides at codon 768 comprises using microarray analysis.

20. The method of claim 18, wherein performing an assay to determine the identity of the nucleotides at codon 768 comprises using a nucleic acid probe that specifically hybridizes with a sequence encoding a S768R mutation.

21. The method of claim 18, wherein the TKI is dasatinib.
22. The method of claim 18, wherein the TKI is nilotinib.
23. The method of claim 18, wherein the TKI is imatinib.
24. The method of claim 18, wherein the TKI is ponatinib.

* * * * *

UNITED STATES PATENT AND TRADEMARK OFFICE
CERTIFICATE OF CORRECTION

PATENT NO. : 9,499,856 B2  
APPLICATION NO. : 13/875079  
DATED : November 22, 2016  
INVENTOR(S) : Matthew Meyerson et al.

Page 1 of 1

It is certified that error appears in the above-identified patent and that said Letters Patent is hereby corrected as shown below:

On the Title Page

Column 1 (Assignee), Line 1, delete "Board" and insert -- Broad --

In the Claims

In column 53, Lines 25-27 (approx.), in Claim 7, after "subject;" delete "comparing the expected amino acid translation with a reference amino acid, wherein the reference amino acid is a serine;"

Signed and Sealed this
Fourteenth Day of February, 2017

Michelle K. Lee
*Director of the United States Patent and Trademark Office*